United States Patent
McSherry et al.

(10) Patent No.: US 6,699,510 B2
(45) Date of Patent: Mar. 2, 2004

(54) ACIDIC AQUEOUS CHLORITE TEAT DIP WITH IMPROVED VISUAL INDICATOR STABILITY, EXTENDED SHELF LIFE, SANITIZING CAPACITY AND TISSUE PROTECTION

(75) Inventors: David D. McSherry, Minneapolis, MN (US); Francis L. Richter, Hugo, MN (US)

(73) Assignee: Ecolab Inc., St. Paul, MN (US)

( * ) Notice: Subject to any disclaimer, the term of this patent is extended or adjusted under 35 U.S.C. 154(b) by 8 days.

(21) Appl. No.: 10/224,300

(22) Filed: Aug. 19, 2002

(65) Prior Publication Data
US 2003/0206971 A1 Nov. 6, 2003

Related U.S. Application Data

(63) Continuation-in-part of application No. 08/938,653, filed on Sep. 26, 1997, now Pat. No. 6,436,444.

(51) Int. Cl.$^7$ .................. A01N 59/00; A01N 59/26; A01N 25/00; A01N 25/24; A01N 37/00

(52) U.S. Cl. .................. 424/665; 424/405; 424/407; 424/409; 424/78.02; 424/78.07; 424/601; 424/605; 424/661; 514/553; 514/557; 514/558; 514/560; 514/568; 514/570; 514/574; 514/576; 514/578; 514/708; 514/709; 514/710; 514/711; 514/769; 514/770; 514/772.1; 514/772.2; 514/777; 514/782; 514/887; 514/944; 514/964; 514/970; 514/588; 510/160; 510/383; 510/419

(58) Field of Search .................. 514/553, 557, 514/558, 560, 568, 570, 574, 576, 578, 708, 709, 710, 711, 769, 770, 772.1, 772.2, 777, 782, 887, 944, 964, 970, 588; 424/405, 407, 409, 78.02, 78.07, 601, 605, 661, 665; 510/160, 383, 419

(56) References Cited

U.S. PATENT DOCUMENTS

| | | | |
|---|---|---|---|
| 2,806,789 A | 9/1957 | Kiser et al. | 514/514 |
| 3,082,146 A | 3/1963 | Wentworth et al. | 162/161 |
| 3,123,521 A | 3/1964 | Wentworth et al. | 424/615 |
| 3,141,821 A | 7/1964 | Compeau | 424/65 |
| 3,147,124 A | 9/1964 | Wentworth | 426/9 |
| 3,227,614 A | 1/1966 | Scheuer | 424/414 |
| 3,728,449 A | 4/1973 | Cantor et al. | 424/671 |
| 3,912,450 A | 10/1975 | Boucher | 422/20 |
| 3,993,777 A | 11/1976 | Coughman et al. | 514/642 |
| 4,025,628 A | 5/1977 | Dewey et al. | 424/44 |
| 4,084,747 A | 4/1978 | Alliger | 422/20 |
| 4,199,602 A | 4/1980 | Lentsch | 514/727 |
| 4,258,056 A | 3/1981 | Lentsch | 514/566 |
| 4,330,531 A | 5/1982 | Alliger | 424/661 |
| 4,376,787 A | 3/1983 | Lentsch et al. | 514/576 |
| 4,404,040 A | 9/1983 | Wang | 134/22.14 |
| RE31,779 E | 12/1984 | Alliger | 252/187.23 |
| 4,891,216 A | 1/1990 | Kross et al. | 424/78 |
| 4,945,110 A | 7/1990 | Brokken et al. | 514/517 |
| 4,986,990 A | 1/1991 | Davidson et al. | 424/665 |
| 5,017,369 A | 5/1991 | Marhevka | 424/78 |
| 404,040 A | 7/1991 | Wang | 134/22.14 |
| 5,185,161 A | 2/1993 | Davidson et al. | 424/665 |
| 5,196,200 A | 3/1993 | Wilson et al. | 424/411 |
| 5,252,343 A | 10/1993 | Kross | 424/661 |
| 5,503,838 A | 4/1996 | Schmidt et al. | 424/407 |
| 5,597,561 A | 1/1997 | Kross | 424/78.07 |
| 5,616,347 A | 4/1997 | Alliger et al. | 424/665 |
| 5,641,498 A | 6/1997 | Loosemore | 424/405 |
| 5,776,479 A | 7/1998 | Pallos et al. | 424/406 |
| 6,039,934 A | 3/2000 | Alliger | 424/53 |
| 6,123,966 A | 9/2000 | Kross | 424/665 |
| 6,203,812 B1 | 3/2001 | Ehrhard et al. | 424/407 |
| 6,524,624 B1 * | 2/2003 | Morelli et al. | 424/665 |

FOREIGN PATENT DOCUMENTS

| | | |
|---|---|---|
| CA | 660515 | 4/1963 |
| DE | 28 00 896 | 7/1978 |
| EP | 0 287 074 A2 | 10/1988 |
| EP | 0 473 395 A1 | 3/1992 |
| EP | 0 530 861 A2 | 3/1993 |
| EP | 0 904 693 A1 | 3/1999 |
| EP | 914833 * | 5/1999 |
| GB | 464330 | 4/1937 |
| WO | WO 81/01516 | 6/1981 |
| WO | WO 89/10747 | 11/1989 |
| WO | WO 96/18300 | 6/1996 |
| WO | WO 99/16418 | 4/1999 |

OTHER PUBLICATIONS

STN Online, American Chemical Society, Columbus, Ohio, Database File: REGISTRY, Registry No. 3844–45–9 (FD&C Blue No. 1), Retrieved on Dec. 12, 2003.*

(List continued on next page.)

Primary Examiner—John Pak
(74) Attorney, Agent, or Firm—Merchant & Gould P.C.

(57) ABSTRACT

The mastitis control teat dip composition having a visible indicator aspect of the invention provides a softening, soothing, smoothing, relaxing property, a rapid initial kill, a useful highly pseudoplastic rheology, a barrier/film-forming capacity, a unique antimicrobial composition that is stable over an extended period of time, and unexpected long term microbial control when compared to the prior art materials disclosed in patents and used in the marketplace. The indicator aspect provides ease of visually detecting the material on the animal skin and can indicate efficacy of the material. The compositions of the invention are made by combining an aqueous liquid composition containing the visual indicator combined with the organic components which can be combined with a simple aqueous solution of a salt of chlorous acid, preferably an alkali metal chlorite. The materials after they are combined and blended into a smooth viscous material containing an emollient package generates active antimicrobial chlorine dioxide and can be immediately contacted with the target animals. The compositions of the invention provide stable visual indication, rapid initial kill, consistent long term kill with chemical and rheological stability.

28 Claims, 8 Drawing Sheets

OTHER PUBLICATIONS

Bennett, R. H., "Teat Dips As A Component Of Coliform Mastitis Control", *Dairy and Food Sanitation*, 2(3):110–114 (Mar. 1982).

Dychdala, G.R., "Acid–Anionic Surfactant Sanitizers", *Disinfection, Sterilization and Preservation, Second Edition*, pp. 253–256 (1977).

Eberhart, R. J. et al., " Germicidal Teat Dip in a Herd with Low Prevalence of *Streptococcus agalactiae* and *Staphylococcus aureus* Mastitis", *J. Dairy Sci.*, pp. 1390–1395 (1983).

ELVANOL Technical Information Bulletin and Material Safety Data Sheet, manufactured by E. I. duPont deNemours & Co. (date unknown).

Flett et al., "pH Affects Bactericidal Action of Detergent", *The American Perfumer & Essential Oil Review* (Dec. 1946).

Flett, L.H., The Antiseptic Properties of Surface Active Agents, *Oil & Soap*, pp. 245–249 (Oct. 1945).

Germicidal Activity of a Chlorine Dioxide Containing Teat Dip, from the 78th Annual Meeting of the IAMFES (International Association of Milk, Food and Environmental Sanitarians), Louisville, KY, USA, Jul. 1991, *Journal of Food Protection*, vol. 54, p. 814 (Oct. 1991).

Gershenfeld, L. et al., Bactericidal and Bacteriostatic Properties of Surface Tension Depressants, *Amer. J. Pharma.*, pp. 306–326 (Aug. 1941).

K–SAN Product Literature, manufactured by KLENZADE PRODUCTS, Division of Economics Laboratory, Inc. (date unknown).

Oliver, S.P. et al., "Prevention of Bovine Mastitis by a Premilking Teat Disinfectant Containing Chlorous Acid and Chlorine Dioxide", *J. Dairy Sci.*, 76(1):287–292 (1993).

The Merck Index, "Tetrazolium Blue," *Merck & Company Incorporated*, 1 pg., (2001).

Schmidt, A. et al., "Evaluation of experimental teat dip containing sodium chlorite and lactic acid by excised teat assay," *J. Dairy Sci.*, vol. 67, No. 12, Abstract, 1 pg. (1984).

* cited by examiner

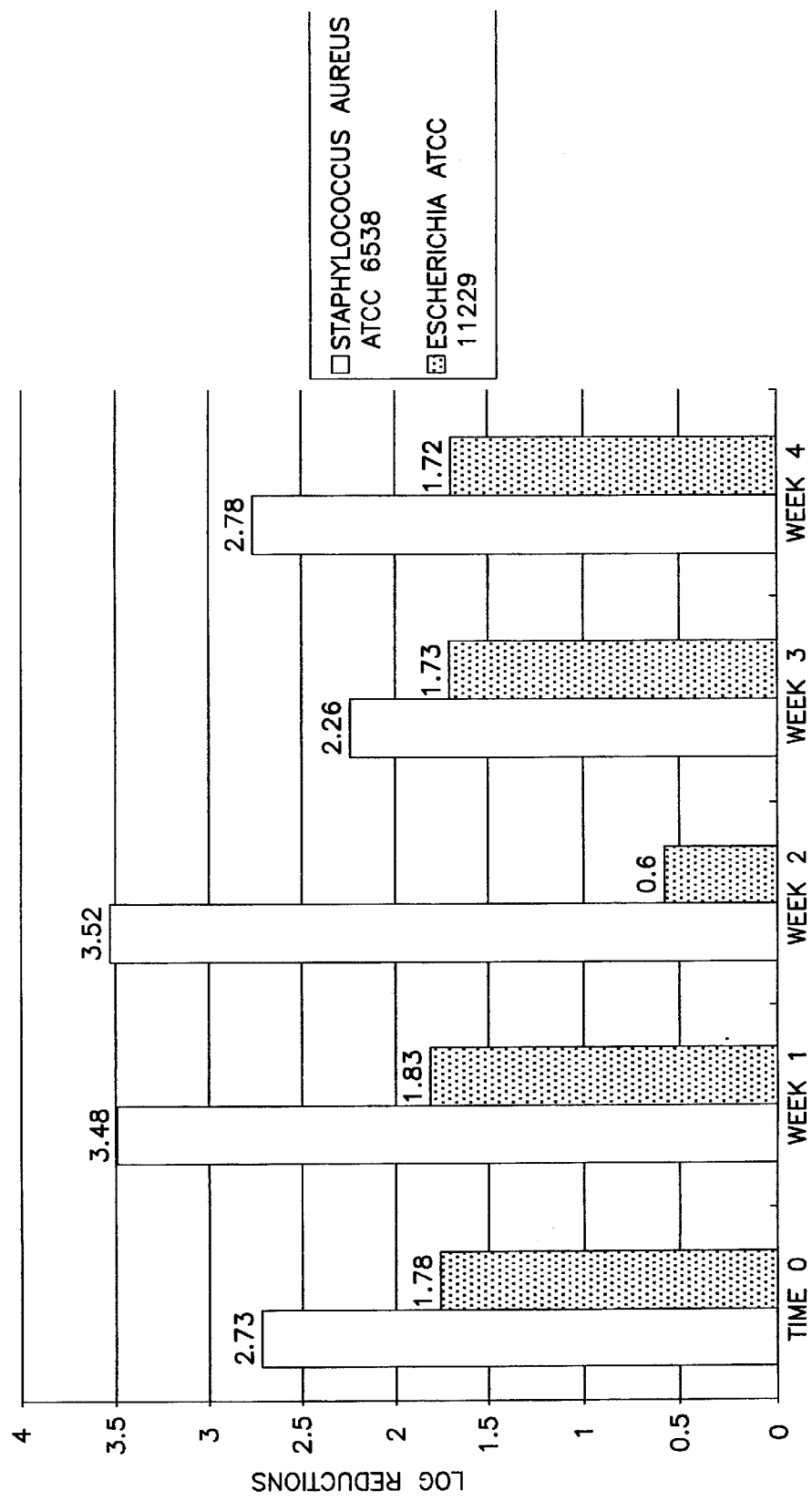

ACIDIC AQUEOUS CHLORITE TEAT DIP WITH IMPROVED VISUAL INDICATOR STABILITY, EXTENDED SHELF LIFE, SANITIZING CAPACITY AND TISSUE PROTECTION

RELATED APPLICATION

This application is a continuation-in-part application of U.S. Ser. No. 08/938,653 filed Sep. 26, 1997 now U.S. Pat. No. 6,436,444.

FIELD OF THE INVENTION

The invention relates to a visually indicating bovine teat dip composition that can be mixed using two parts, a simple chlorite solution and an acid or acidulant formulation, to form a stable, effective composition that can be used in routine dairy procedures.

BACKGROUND OF THE INVENTION

Bovine mastitis is the most common and most costly disease affecting dairy herds. Some estimates suggested at least half of the dairy animal population have some degree or form of mastitis. This condition results in lowered milk yield and reduced quality. Economic loss to mastitis in the U.S. is estimated at about $1.8 billion or approximately 10% of total milk sales with about two-thirds of this loss due to reduced milk production from infected cows. Mastitis is an inflammation of the mammary gland. Similarly, inflammation is one response of a tissue or organ to insult or injury. An injury caused by physical, chemical or thermal trauma can produce an inflammatory response. In the dairy cow, mastitis typically results from microorganisms, usually bacteria, that invade the udder, multiply in the delicate milk producing tissues, and synthesize toxins, a by-product of bacterial metabolism. The characteristic features of inflammation are swelling, heat, redness, pain and disturbed function.

While the animal immune system can fight intramammary infections, many chronic infections remain sub-clinical (asymptomatic) and undetected unless diagnosed by laboratory testing. Sub-clinical mastitis can result in a reservoir of micro-organisms that leads to the infection of other animals within the herd. More than 80 species of microorganisms have been identified as causal agents, although approximately 95% of mastitis is caused by four pathogens; *Staphylococcus aureus, Streptococcus agalactiae, Streptococcus dysagalactiae,* and *Streptococcus uberis*. Mastitis causing pathogens fall into two categories namely contagious and environmental. Contagious bacteria, such as *Streptococcus agalactiae* and *Staphylococcus aureus*, primarily colonize host tissue sites such as mammary glands, teat canals, teat skin lesions etc. and are spread from one infected cow to another during the milking process. Environmental bacteria, often streptococci, enterococci and coliform organisms, are commonly present within the cow's surroundings from sources such as cow feces, soil, plant material, bedding or water, and infect by casual opportunistic contact with an animal during the inter-milking period. This distinction, although not exclusive, is of practical importance because different dairy herd maintenance measures are needed for the different groups of microorganisms. In all bovine mastitis cases, whatever the causal microorganism, the route of transmission of the invading pathogen into the inner gland of the udder is through the teat orifice and teat canal.

Management of dairy herds focuses attention on treatment of both established mastitis and on prevention of new intramammary infections. Therapy and hygiene are the two fundamental components of an effective mastitis control protocol. Each is applied in concert, and each operates independently. The primary effect of therapy is to increase the rate of eliminating established infections; whereas, hygiene reduces the frequency of infection by interrupting transmission vectors. We cannot present all ancillary factors that may be employed for the elimination and prevention of mastitis, however, the most effective therapy and hygiene practices are, respectively, antibiotic infusion treatment of the udder's four quarters at the end of lactation; and, post-milking teat antisepsis or "teat dipping" during lactation.

Researchers agree, and an abundance of published evidence supports the concept, that dipping teats into an effective antimicrobial solution immediately after each milking is the single most effective procedure for decreasing new intramammary infections in lactating cows. Between 1955 to 1970, Dodd and co-workers (F. K. Neave, F. H. Dodd, and R. G. Kingwell, 1966, "A Method of Controlling Udder Disease", Vet. Rec. 78:521; F. K. Neave, F. H. Dodd, R. G. Kingwell and D. R. Westgarth, 1969, "Control of Mastitis in the Dairy Herd by Hygiene and Management", J. Dairy Sci. 52:696; F. H. Dodd, D. R. Westgarth, F. K. Neave and R. G. Kingwill, 1969, "Mastitis—The Strategy of Control", J. Dairy Sci. 52:689; and F. H. Dodd, and F. K. Neave, 1970, "Mastitis Control", Proceedings, Nat'l. Inst. Res. Dairying, pp. 21–60) conducted extensive epidemiologic investigations in commercial dairy herds. From this work, they developed the conceptual basis for modern mastitis control methods of which teat dipping is an integral component. The efficacy and value of teat dipping has since been confirmed in dozens of field trials, and it is now accepted that an effective teat dip can reduce the incidence of new intramammary infections at least 50% and often up to 90%.

To reduce mastitis, commercial teat dips have been developed containing a variety of antimicrobial agents including iodophors, quaternary ammonium compounds, chlorhexidine salts, chlorine release compounds (e.g. alkali hypochlorites), oxidizing compounds (e.g. hydrogen peroxide, peracids), protonated carboxylic acids (e.g. heptanoic, octanoic, nonanoic, decanoic, undecanoic acids), acid anionics (e.g. alkylaryl sulfonic acids), and chlorine dioxide (from chlorite). These agents, which have varying degrees of effectiveness, limit the transmission of mastitis by reducing pathogen populations on the teat. Teat dips, can also be divided into two broad classifications. The Class I type are antimicrobial and are applied to kill microorganisms already present in the teat canal or on the surface of the teat skin. By design, their microbiological effect is immediate and their targets primarily the contagious organisms that are vectored between animals during the pre-milking, milking and post milking process. The Class II type teat dip, often referred to as a "teat sealer," is a film-forming or coating composition which may or may not be antimicrobial; and, functions by developing a residual protective barrier on the teat thus providing prophylaxis by sealing the teat off from its environment. The film which forms on the surface of the teat serves as a physical barrier through which mastitis causing pathogens cannot penetrate during the inter-milking period.

General disclosures of teat dip technology are shown in: "Current Concepts of Bovine Mastitis." 1996, Fourth Ed. National Mastitis Council, Madison Wis.; P. A. Murdough and J. W. Pankey, 1993. "Evaluation of 57 Teat Sanitizers Using Excised Cow Teats", J. Dairy Sci. 76:2033–2038; J. W. Pankey et al., 1984, "Uptake on Post-milking Teat Antiseptics", J. Dairy Sci. 67:1336–1353; R. J. Farnsworth, 1980, "Role of Teat Dips in Mastitis Control", J. Am. Vet. Med. Assoc. 76:1116–1118; W. N. Philpot, 1979, "Control of Mastitis by Hygiene and Therapy", J. Dairy Sci. 62:168–176; W. N. Philpot and J. W. Pankey, 1978, "Hygiene in the Prevention of Udder Infections V. Efficacy of Teat Dips Under Experimental Exposure to Mastitis Pathogens", J. Dairy Sci. 61:956–963; R. P. Natzke, 1977, "Role of Teat Dips and Hygiene is Mastitis Control", J. Amer. Vet. Med. Assoc. 170:1196–1198; W. N. Philpot and J. W. Pankey, 1975, "Hygiene in the Prevention of Udder Infections. III. Effectiveness of 59 Teat Dips for Reducing Bacterial Populations on Teat Skin", J. Dairy Sci. 58:209–216; R. J. Eberhart and J. M. Buckalew, 1972, "Evaluation of a Hygiene and Dry Period Therapy Program for Mastitis Control", J. Dairy Sci. 55:1683–1691; W. D. Schultze and J. W. Smith, 1972, "Effectiveness of Postmilking Teat Dips", J. Dairy Sci. 55:426–431; D. P. Wesen and L. H. Schultz, 1970, "Effectiveness of a Post-Milking Teat Dip in Preventing New Udder Infections", J. Dairy Sci. 53:1391–1403; and British Pat. No. 1,144,637 (Kelco Chemicals Ltd.), published Mar. 5, 1969. U.S. Pat. No. 4,199,602 (Lentsch) issued Apr. 22, 1980, U.S. Pat. No. 4,258,056 (Lentsch) issued Mar. 24, 1981; and U.S. Pat. No. 4,376,787 (Lentsch) issued Mar. 15, 1983 disclose nitroalkanol, amino carboxylate/sulfonate, and sulfonate based compositions. U.S. Pat. No. 4,446,153 (Yang) issued May 1, 1984 discloses a benzyl alcohol/phenyl ethanol based composition.

Typical disclosures of intermilking or protective (barrier-type) film-forming teat dips or teat "sealers" can be found in Akers et. al., U.S. Pat. No. 3,066,071, issued Nov. 27, 1962; Kraus, U.S. Pat. No. 3,222,252, issued Dec. 7, 1965 (but, see Philpot et. al., J. Dairy Science 58:205–216); Coughman and Brown, U.S. Pat. No. 3,993,777, issued Nov. 23, 1976; Pugliese, U.S. Pat. No. 4,049,830, issued Sep. 20, 1977; and Andrews et al., U.S. Pat. No. 4,113,854, issued Sep. 12, 1978. A teat sealer similar or identical to the Andrews et. al. film-forming composition is in commercial use and has been discussed in the dairy science literature. See, for example, R. J. Farnsworth et. al., 1980, "Use of a Teat Sealer for Prevention of Intramammary Infections in Lactating Cows", J. Am. Vet. Med. Assoc. 177:441–444; and R. J. Farnsworth et. al., 1981, "The Effect of a Teat Sealer on Coliform Mastitis", The Bovine Practitioner, No. 16, pp. 28–29. Still further examples of barrier-type film-formers for bovine teats can be found in Silver et al., U.S. Pat. No. 4,199,564, issued Apr. 22, 1980; Dybas et al., U.S. Pat. No. 4,311,709, issued Jan. 19, 1982; Marhavka , U.S. Pat. No. 5,017,369, issued May 21, 1991; and Schmidt et al., U.S. Pat. No. 5,503,838, issued Apr. 2, 1996.

Persons skilled in the art of bovine mastitis treatment know that antimicrobial teat dip compositions (Class I type) which do not form protective films with barrier properties have a shortened residual time on the teat and their efficacy is quickly lost due to adsorption, ion-pairing, oxidation or simply sloughing off. Furthermore, such teat dips often fail to retard the entrance of bacteria into the teat canal during the intermilking period and provide no protection to the teat from irritation caused by wind, sun or contact abrasion. As disclosed in the art, attempts have been made to provide antimicrobial teat dips containing film-forming materials designed to form protective barriers on the skins of the teats; and, to afford continuous protection against mastitis causing pathogens, both contagious and environmental, and, from irritation caused by exposure to adverse environmental elements.

Early researchers discovered that incorporating a film-forming, protective barrier system into an antimicrobial teat dip was fraught with technical problems, either physicochemical problems with the composition or application/performance problems in practice. The best prophylactic barriers, and most environmentally durable, are water insoluble synthetic organics made up of homopolymers or heteropolymers of two or more different monomers. These are applied either from volatile solvent based compositions or by film-forming polymer latexes which are suspensions of a water insoluble polymer in water. U.S. Pat. No. 3,066,071 typifies the former type; and U.S. Pat. No. 4,113,854 discloses compositions typical of the latter kind. Typically, barrier films formed upon teats when applied from a volatile solvent based mastitis dip composition are not user, animal or environmentally friendly. In practice, these materials subject the skin of the teat to the drying, irritating effects of organic solvents. Compositions containing a film-forming polymer latex overcome volatile solvent concerns as polymer latexes are most often suspensions of a water insoluble polymer(s) in water; however, commercial latexes necessarily include stabilizers, preservatives, suspending agents etc. which add complexity; and, as such are frequently incompatible with the most preferred and most efficacious antimicrobial agents. All water insoluble polymeric films, which generally form a flexible almost rubbery film on the teat skin, must be removed by peeling. In practice, such mastitis control compositions have not received widespread acceptance because of the inconvenient, time-consuming, often troublesome removal process prior to milking.

U.S. Pat. No. 3,222,252 describes a bovine teat dip consisting of vegetable oils of the drying or semi-drying types and certain fatty acid esters. In concept, this disclosure bridges the gap between synthetic polymer coatings and natural polymer coatings. In practice, oil based dips have proved to be ineffective in preventing mastitis, and they are difficult to remove from the teats. In fact, their use has tended to increase the incidence of mastitis (see Philpot et. al, J. Dairy Science 58:205–216).

U.S. Pat. No. 3,993,777, referenced above, discloses an aqueous thickened quat based formulation of high viscosity containing emollients such as lanolin and glycerin. The material forms a protective film and bacteriostatic barrier about the teat which is easily removed by washing; thus, transitioning from water insoluble protective films which in practice are peeled from the teat to water washable films. However, the shortfall of this teaching is the use of hydroxyethylcellulose employed as a thickener (its most typical function) in the preferred formulation which, by chance, has the characteristic of forming pliable non-brittle films upon drying. In herd practice, such cellulosic thickeners seldom perform the dual-function role of providing a tenacious barrier, being too readily removed because of its water-sensitivity, wherein the performance of the antimicrobial barrier is lost. U.S. Pat. No. 4,311,709 also discloses a film-forming methycellulose having similar disadvantage as a teat dip barrier. U.S. Pat. No. 4,049,830 discloses a bovine teat dip composition which delivers an oil-in-water emulsion to the teat and, upon drying, forms an antimicrobial lipid solids barrier which remains soft and tacky for prolonged periods and is water washable. Herd experience has shown that soft barriers are too easily abraded or otherwise sloughed off during the intermilking period with subsequent reduction or loss of biocidal function. U.S. Pat. No. 5,017,369 discloses antimicrobial mastitis treatment compositions which utilize a water resistant film-forming agent, polyvinyl alcohol. This art teaches away from incorporation and use of thickener admixtures, suggesting that adequate viscosity can be obtained simply by adjusting the amount of polyvinyl alcohol in the composition. Such compositions are, in application, at commercial disadvantage because polyvinyl alcohol by itself does not provide effective teat cling nor does it decrease the mobility of the dipping liquid which is manifested by excessive drain-off and loss of product; and, therefore significant reduction of barrier function and microbial performance. U.S. Pat. No. 5,503,838 overcomes this disadvantage in disclosing antimicrobial teat dip compositions containing polyvinyl alcohol in cooperation with thickening agents such as a xanthan gum. Unfortunately, neither U.S. Pat. No. 5,017,369 which typically embodies chlorhexidene gluconate or quaternary ammonium compounds as the antimicrobial; nor, U.S. Pat. No. 5,503,838 which uses iodine as the preferred biocidal agent, address the issue of teat dermal irritation caused by residual barrier films containing resident, chemically aggressive, often toxic, antimicrobial agents which remain on skin contact for extended periods of time.

Alliger, U.S. Pat. No. Re. 31,779, reissued Dec. 25, 1984; Alliger, U.S. Pat. No. 4,330,531 (Alliger) issued May 18, 1982; Kross et al., U.S. Pat. No. 4,891,216, issued Jan. 2, 1990; Davidson et al., U.S. Pat. No. 4,986,990, issued Jan. 22, 1991; Davidson et al., U.S. Pat. No. 5,185,161, issued Feb. 9, 1993; and Kross, U.S. Pat. No. 5,597,561 disclose technology embodied in a commercial composition sold as an antimicrobial barrier teat dip under the name UDDER-GOLD PLUS (Alcide Corp., Redmond, Wash.). The patents disclose two aqueous solutions, described as gels, adapted to be mixed in a 50/50 proportion wherein (according to patent and product literature) chlorous acid/chlorine dioxide are generated by chemical reaction of I-hydroxy-benzene-acetic acid (mandelic acid) and sodium chlorite present in first and second gels respectively. The second gel can contain a thickener. Later patents disclose a homopolymer of 2-acrylamido-2-methylpropane sulfonic acid (polysulfonic acid) which forms a protective film over the teat. Although this composition has proven effective, it is not without problem. The herdsman is advised to mix and use the admixture for only one herd milking, discarding any extra. This attribute is likely a consequence of chlorine dioxide loss (hence, loss of antimicrobial efficacy) either from chemical incompatibility and/or off-gassing. The polysulfonic acid "gelling agent" does not immobilize the treatment on the teat and significant drippage/waste occurs. U.S. Pat. No. 5,597,561 teaches that polysulfonic acid has proven problematic because of its strong affinity to the dermal tissue and tendency to form a solid matrix which is difficult to remove by washing.

Richter, U.S. Ser. Nos. 08/038,064 and 08/038,553, and U.S. Pat. No. 6,379,685, disclose basic teat dip technology. These systems are two part chlorite and acid materials that when blended form a protective layer or coating. The utility or effectiveness of these systems can be enhanced by the presence of a marker dye showing the location of the treatment on or adhering to the animal. Simply including a dye in the chlorite part, however, or in the combined materials, is often not fully effective. The oxidizing nature of chlorite ($ClO_2^{-1}$) or chlorine dioxide ($ClO_2$) can rapidly alter or bleach the typical added color.

A substantial need remains after all these attempts, for long lasting protective, film or shield forming barrier-type teat dip compositions having a visual indicator or unique color that can indicate the presence of an immediate and long lasting antimicrobial effect against a wide spectrum of mastitis causing organisms. The visual indicator can also indicate the presence of an active effective amount of $ClO_2$.

BRIEF DESCRIPTIONS OF THE INVENTION

We have discovered a mastitis control treatment having important functional properties that are uniquely combined into one composition. The compositions of the invention can contain a visual indicator material. Such an indicator material can be useful in blending the material to show the presence of an active chlorine dioxide component, can be used to demonstrate the location of the material on the animal skin, can be used as an indication of active chlorine dioxide in the material formed on the animal skin, or can be an indicator of the presence of active material in the blended composition showing an extended shelf life after blending. Such a visual indicator material can be prepared using one of a number of options. First, urea has been found to stabilize the dye blended into the overall composition or included in the acid or organic phase of the composition. The urea material used to stabilize the dye has also been shown to modulate the production and/or release of chlorine dioxide by the blended material. The teat dip material provides a reduced rate of release of the chlorine dioxide into the active blend, thus somewhat reducing the effective concentration of the chlorine dioxide in the material but greatly extending the lifetime of the material having an effective concentration of chlorine dioxide. In this way, wasteful production of chlorine dioxide does not occur while the delayed production of the chlorine dioxide maintains a lower, but more efficient concentration of chlorine dioxide in the material formed on the animal skin. A second embodiment of the invention involves a dye or combination of dyes that show that the sodium chlorite part is blended with the acid part and has been blended to a uniform active composition. A dye or blend of dyes can be used to produce a color change in the resulting blended material. In one embodiment, a pH sensitive dye can be included in the acid part that is converted to a different color by the change in pH as the sodium chlorite part is blended with the acid part. The pH of the original acid part is typically approximately 2.7, while the pH of the blended part is typically greater than 3.0. Such a color change can be helpful. Such a color change can be produced using a single stable dye or a stable dye blended with a relatively unstable dye effectively showing a visual dramatic color change upon blending. A further embodiment of the invention involves dispersing a dye or pigment in an oil phase. The oil phase containing the dye can maintain the dye in a separate phase apart from the oxidative material in the aqueous blended phase. One aspect of this embodiment involves the use of a "drying oil" that, in the presence of oxidative systems, can crosslink to substantially increase the viscosity of the oil phase, thus substantially reducing the tendency of the dye to be leached from the oil phase into the aqueous phase. Maintaining the dye in the oil phase protects the dye from aqueous oxidation by the oxidative systems. A last embodiment of the visual indicator of the invention is a chemiluminescent material that can be used. The chemiluminescent material involves materials that can be blended to produce the characteristic soft glow produced by chemiluminescence. The compositions would be formulated such that the chemiluminescent glow is produced only upon blending and would continue to glow only as long as an effective concentration of oxidant remained in the composition. Such a glow would provide an indication to the blender that the composition was uniformly blended and that the composition maintained a high level of activity for an extended period of time. The glow would tend to subside as the active material dropped in concentration upon storage.

The first embodiment of the invention provides a stable visual indicator or color using a dye or a mixture of dyes.

The dye color is maintained by one of the disclosed stability systems. The dye stability can be the result of the use of either a stabilizing amount of urea, the use of chemiluminescent systems that are activated by an oxidant or the dye can be incorporated into a non-aqueous phase and maintained apart from the oxidative nature of the chlorine species in aqueous solution. The stable indicated materials of the invention also provide a soothing softening emollient character, rapid initial kill, long lasting antimicrobial activity, a stable chemistry and rheology. The blend of lanolin composition and polyhydroxy emollients provide enhanced softening, smoothing, soothing character to treated skin. The compositions of the invention possess favorable rheology that promotes cling and immobilizes the mastitis treatment on the teat. The composition develops a barrier giving prophylactic protection and containing at least one resident agent for continuous biocidal protection. The composition does not cause dermal irritation and, is removable by a simple water-washing technique. The barrier has sufficient adherence to withstand premature loss of integrity due to abrasion of environmental conditions. Compositions of this invention are mastitis control and prevention treatments often described as "teat dips," though of course methods of topical aseptic application other than immersion or "flooding" might be used by the herdsman; for example, spraying, brushing, swabbing or foaming onto the teats. When employed as a teat dip, which is a particularly effective practice of application, the teats of the animal are dipped into a reservoir or receptacle containing a composition of the present invention; whereupon, the source is removed, and, preferably one-half to three-fourths of the distal teat has been coated with treatment. After application (by whatever method), the resident treatment adheres onto the teat until drying occurs and development of a protective film results which provides an antimicrobial barrier and prophylactic shield thus protecting the teat from pathogens and adverse environmental factors.

The mastitis control compositions of the invention comprise components dissolved or suspended in an aqueous carrier or medium. The components of the compositions include a chlorine dioxide generating chemical such as sodium chlorite, an acidulant that can contain a protic acid component and an active antimicrobial acid component, an organic film-forming agent, rheology modifying materials, a hydrotrope, an emollient, a surfactant, a buffer if needed, a colorant and other optional materials.

A pseudoplastic aqueous rheology is effected in the composition of the invention by admixtures of polymeric materials such as a xanthan gum and polyvinyl alcohol compositions. When shear stress is applied to the composition (i.e., dipping), product viscosity is reduced allowing easy and rapid application to the teat; and, upon the release of shear (i.e., removal of source), total viscosity recovery occurs almost instantaneously immobilizing the coating, providing cling and assuring little waste by drippage. Further, said compositions have little or no viscoelastic character which thus allows the treatment to flow and to coat the teat smoothly, forming a continuous efficacious layer over the skin of the teat without formation of mucilage streamers as the applicator is withdrawn. The compositions flow slightly down the teat following application to form a thicker layer or "plug" across the orifice of the teat canal; and, thus cause a more effective prophylactic barrier against bacteria entering the teat canal.

An occlusive polymeric barrier/film-forming attribute is contributed by inclusion of intermediate or fully hydrolyzed polyvinyl alcohol. Carefully composed polyvinyl alcohol compositions of this invention provide to the mastitis control treatment, after drying, a balanced barrier layer which remains pliable and maintains integrity on the teat; which can be rendered antimicrobial by envelopment of biocidal agents; which does not cause irritation; and, which provides significantly improved and prolonged protection to the teat during the intermilking period by structured adherence, yet does not sacrifice ease of removal prior to milking.

A unique preferred antimicrobial composition is accomplished that can contain one fugitive biocidal agent, chlorine dioxide, and one or more non-fugitive acid biocidal agents such as a $C_{6-12}$ carboxylic acid, including heptanoic acid, pelargonic acid (nonanoic acid), etc.; an anionic sulfonate, including dodecylbenzenesulfonic acid, and other acidic antimicrobials and mixtures thereof. Such admixtures provide superior cooperative antimicrobial effect. The combined agents provide an immediate, additive biocidal action to contagious mastitis causing pathogens present on the teat when the composition is first applied. A continuous, longer term antimicrobial action is afforded by the non-volatile agents which become enveloped into the barrier film upon drying. Chlorine dioxide, formed in situ by reacting ingredients within the composition, is present only during the initial application of treatment onto the teat and can off-gas during treatment dry-down. This effect is advantageous because the superior antimicrobial properties of chlorine diodide are utilized to destroy the pathogens of greatest concern to the herdsman, i.e., the contagious mastitis causing organisms already on the teat and in the distal teat canal orifice; but, once applied, chlorine dioxide dissipates and thus removes the potential for severe teat skin irritation which otherwise might result from this very reactive chemical; and, for any incidental residuals in the producers milk. Heptanoic acid or nonanoic (pelargonic) acid, which are preferred antimicrobial agents within compositions of the present invention, and/or dodecylbenzenesulfonic acid, all being of non-volatile character, augment the biocidal performance of chlorine dioxide upon initial application; and, as treatment drying occurs with subsequent barrier formation, become resident within the prophylactic coating wherein the agents provide continuous and efficacious antimicrobial protection from mastitis causing environmental organisms. After the chlorine dioxide component, made in situ by the combination of the aqueous acidulant part with the aqueous chlorite part, becomes volatilized and is thus removed from the composition, the composition maintains extended antimicrobial activity and the composition maintains an effective barrier, including a milk duct plug, to environmental pathogens and soils.

Surprising and unexpected long term chlorine dioxide residence and chemical stability results in practice which is in distinct contrast to commercial embodiments of prior art, specifically and particularly the commercial antimicrobial teat dip sold under the name UDDER-GOLD PLUS (Alcide Corp. Redmond, Wash.), having affixed use instructions which advise the user to blend, in equal proportions, only sufficient admixture of cooperative parts (UDDER-GOLD PLUS BASE and UDDER-GOLD PLUS ACTIVATOR) for one herd milking—discarding any remainder.

We have discovered that preferred mastitis treatment compositions of this invention, once having formed chlorine dioxide in situ from chemical reactants blended together by the herdsman in preassigned proportion, retain this antimicrobial agent and associated antimicrobial property within the admixed teat treatment for extended periods of time. A typical useful application life span of such product being approximately one month following preparatory blending.

We believe this unusual chlorine dioxide stability is an additional consequence of the Theological properties of the preferred compositions whereby the chlorine dioxide gas is entrapped and held homogeneously dispersed throughout the product. Such attribute has many practical advantages for the herdsman including convenience of preblending large mixtures of teat treatment and eliminating need for repeatedly preparing the exact quantity applied at each milking, reducing wasteful and costly disposal of unused, but unstable product which cannot be saved for next milking; and, enhanced safety for the user who would otherwise be exposed to off-gassing chlorine dioxide fumes during the milking process.

The compositions of the invention comprise an admixture comprised of two cooperative parts: The first part, of major or equal proportion, having, in aqueous liquid mixture, an acid component and the plurality of components used in the mastitis control compositions of this invention and including all ingredients of organic structure including rheology modifiers and thickeners; emollients, humectants, conditioners and medicaments; surfactants and hydrotropes; antimicrobial agents and preservatives; buffers, acidulants; chromophores and the like: The second part, of equal or minor proportion, being a chlorous acid or salt thereof, more specifically, an alkali metal chlorite; being of aqueous liquid, particulate-powder, or compressed or cast molten solid form; and, generally in practice, added to the first part of the admixture. Further, the aforementioned second part must, if liquid, be readily miscible or, if solid, be easily soluble within the first part to effect rapid homogeneous blending which is of particular importance when large quantities of this admixture are prepared on site by the herdsman. Experience has taught that favorable admixture blending is best accomplished by liquids of the second part having no ordered structure, i.e. no thickened or gelled character; and, by solids of the second part having large surface area. In practice, this means liquids having fluid characteristics similar to water, and solids having particulate form.

The primary function of the second part is to carry the chlorine dioxide release agent into the admixture of this mastitis control treatment; however, lesser adjuvants may be included within, e.g., alkali metal carbonate salts added to commercial chlorite solutions to improve stability. Such lesser adjuvants must not alter, to any appreciable degree, rheology properties of the second part other than characteristic of the aqueous carrier itself. Once joined, the alkaline chlorine (III)/chlorite composition of the second part is blended into the acidic solution of the first part with resulting admixture having a buffered pH of approximately 3.0; whereupon, and by chemical reaction well known in the scientific art and literature, the disproportionation of chlorine (III)/chlorite occurs with a measured rate of formation of chlorine dioxide. Because this reaction begins immediately and because only very small quantities of chlorine dioxide are required for pronounced microbiocidal effect, the thus prepared mastitis control treatment is ready for application as soon as needed.

Commercial compositions of the invention are held within a user friendly dual or "duet" packaging combination designed to contain and transport parts A and B of these compositions together in predetermined and premeasured proportions and to be cooperative in the blending process wherein the user pours or otherwise causes the entire contents of package B, an equal or minor proportion, to be discharged into package A, an equal or major proportion, which then becomes the container and holding device for the admixture or final mastitis control treatment. The unique visual indicator or color stability maintains effective antimastitis protection by maintaining $ClO_2$ activity while also maintaining a visual indicator or color.

BRIEF DISCUSSION OF THE DRAWINGS

FIGS. 1A, 1B, 1C, 1D, 2A and 2B are graphical representations of the test data and comparisons shown in the tables of data in the application.

FIG. 1A is a four week biocidal efficacy analysis of Example II using the food contact sanitizing protocol. FIG. 1B is a four week biocidal efficacy analysis of Example II using the food contact sanitizing protocol with a 10% milk challenge. FIGS. 1C and 1D detail four week biocidal efficacy analyses of the UDDER GOLD PLUS formulation obtained under similar conditions as the data in FIGS. 1A and 1B respectively.

FIG. 2B is a four week efficacy analysis of Example II using the procein skin test protocol.

DETAILED DESCRIPTION OF THE INVENTION

Figure 1A:
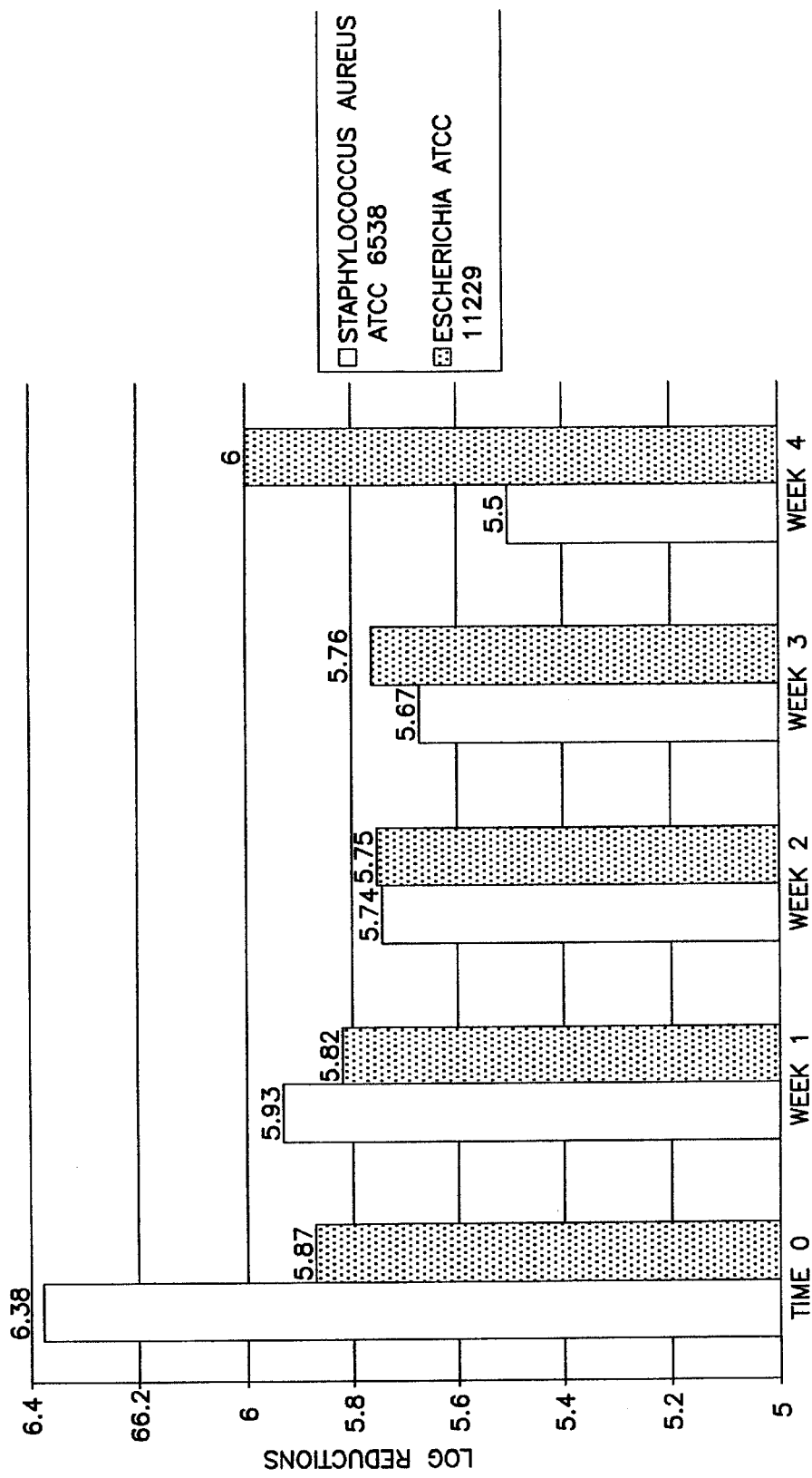

Components Used in the Mastitis Control Compositions of this Invention

Dyes useful in formulating the antimastitis compositions of the invention include both water soluble and water insoluble dyes. Water soluble dyes can be formulated easily in the aqueous systems of the invention. Water insoluble dyes can be included in an oil phase that can be dispersed or suspended in either of the parts of the antimastitis materials of the invention, however, preferably the oil is dispersed in the acid part and maintained separate from the chlorite part until use. Useful dyes for the purpose of this invention are typically organic compounds that absorb visible light resulting in the appearance of a detectable color. Such organic dyes are useful in the teat dips of the invention but should have minimal toxicity since they are in contact with milk producing organs of the dairy animals. In this regard, common FD&C approved dyes are used since these materials are typically approved for use as direct additives for food stuffs. The dyes typically useful in this invention are colorants approved for use in foods, drugs, cosmetics and medical devices.

Colorants currently in use and their status follow. Colorants permitted in foods that are (1) subject to certification: FD&C Blue No. 1, FD&C Blue No. 2, FD&C Green No. 3, FD&C Red No. 3, FD&C Red No. 40, FD&C Yellow No. 5, FD&C Yellow No. 6, Citrus Red No. 2, and Orange (B) (2) exempt from certification: annatto extract, θ-apo-8'-carotenal, canthaxanthin, caramel, θ-carotene, carrot oil, cochineal extract (carmine), corn endosperm oil, dehydrated beets (beet powder), dried algae meal, ferrous gluconate, fruit juice, grape color extract, grape skin extract, paprika, paprika oleoresin, riboflavin, saffron, synthetic iron oxide, tagetes meal and extract, titanium dioxide, toasted partially defatted cooked cottonseed flour, turmeric, termeric oleoresin, ultramarine blue, and vegetable juice. Colorants permitted in drugs (including colorants permitted in foods) that are (1) subject to certification: FD&C Red No. 4, D&C Blue No. 4, D&C Blue No. 9, D&C Green No. 5, D&C Green No. 6, D&C Green No. 8, D&C Orange No. 4, D&C Orange No. 5, D&C Orange No. 10, D&C Orange No. 11, D&C Red No. 6, D&C Red No. 7, D&C Red No. 17, D&C Red No. 21, D&C Red No. 22, D&C Red No. 27, D&C Red No. 28, D&C Red No. 30, D&C Red No. 31, D&C Red No. 33, D&C Red No. 34, D&C Red No. 36, D&C Red No. 39, D&C Violet No. 2, D&C Yellow No. 7, D&C Yellow No. 8, D&C Yellow No. 10, D&C Yellow No. 11, and Ext. D&C Yellow No. 7. Additionally cantaxanthin, beta carotene, chlorophyllin, and other colors are known.

Often the process and use to formulate the antimastitis compositions of the invention, the pH and other variables in the composition can have a large impact on color stability. Not only will the oxidative effects of the chlorine species present in solution tend to reduce the color, but exposure to light, heat, air and other variables in the environment can also add to color instability. For a more detailed listing and/or discussion on approved colors, please see D. M. Marmion, *Handbook of U.S. Colorants, Foods, Drugs, Cosmetics and Medical Devices*, John Wiley & Sons Inc., New York (1991) and *U.S. Code of Federal Regulations*, Title 21, parts 70–82.

We have found two mechanisms that can aid in the stability of the dyes used as marker indicators for the antimastitis compositions of the invention. We have found that the acid part of the antimastitis compositions of the invention can be formulated with a color stabilizing amount of urea in combination with an effective marking amount of dye to form an acid part that has stable color. Further, when combined with the chlorite part to form a fully formulated composition, the urea is effective to maintain stable color for an extended period of time. In the absence of urea, typical organic dyes containing an oxidizable structure having a number of aromatic unsaturation and coordinated covalent unsaturation, can be stabilized. We have found that using about 0.1 to about 5 wt % of urea, in the acid part (about 0.1 to about 5 wt % of urea in the total formulated composition), preferably about 0.5 to 3 wt % (about 0.5 to about 3 wt % based on the total formulated composition) can provide excellent extended color stability for the marker dye in the fully formulated antimastitis composition.

Alternatively, we have found that by incorporating the marker dye in a non-aqueous phase that is dispersed into the acid part or into the final combined teat dip material upon blending, can help maintain the color stability of the dye. A dye material that is soluble in the non-aqueous phase is selected and is then dissolved into the non-aqueous phase. Such a colored phase is maintained in a separate "part 3" of the composition and is then blended after the acid part and the chlorite parts are combined just before use. After addition to the combined parts, the material is agitated to ensure that the oil or the non-aqueous phase is uniformly dispersed in a fine particle size throughout the teat dip composition, thus providing excellent marker properties for the combined material. Alternatively, the non-aqueous phase can be carefully dispersed into the acid part such that it is present in a finely divided particulate form prior to combining the acid phase with a chlorite part to form the final material. The acid part can be agitated to ensure the uniform dispersion of the colored non-aqueous phase throughout the acid phase before combination or the entire formulation can be carefully agitated to ensure that the non-aqueous phase is uniformly dispersed throughout to provide an excellent marking property.

Virtually any non-aqueous medium can be used as a vehicle for the colorant. The important criterion for selection of the non-aqueous medium is its limited solubility in the aqueous media of the acidulant or acid part and the aqueous chlorite part. Further, the non-aqueous material has to be a substantial solvent for the colorant material. Such a non-aqueous phase must have the capacity to dissolve or suspend in an effective form up to 5 wt % of the dye based on the non-aqueous phase. Such an amount will be useful to act as a position indicator for the combined antimastitis compositions of the invention.

Preferred non-aqueous materials for use in the invention are oily materials that have substantially limited aqueous solubility. Such oil materials can comprise both natural and petroleum oils. Such oils can be substantially saturated oils having little olefinic unsaturation or can have substantial olefinic unsaturation. Natural oils that can be used include oily materials, substantial liquids at room temperature, derived from both animal and plant sources. Further synthetic and petroleum oils can also be used. Synthetic oils typically comprise polyol esters of diacid materials, or olefin oligomers. Petroleum oils are typical oils derived from petroleum sources and refined leaving a substantially higher carbon material substantially free of waxes but containing substantial proportions of hydrocarbon molecules. These materials can be substantially saturated or can have substantial unsaturation.

A preferred natural oil for use in forming a stable colorant of the invention comprises forming the non-aqueous phase comprising a substantial proportion of a drying oil. The use of a drying oil can aid in forming barrier layers in the invention since the drying oils can help form a film when exposed to the air or upon exposure to oxidizers present in the liquid phase, i.e. chlorite or chlorous acid. Drying oils oxidize upon exposure to the air from a liquid film to a substantially solid dry film. Both synthetic and natural drying oils can be obtained, however, natural oils are preferred. Both natural and synthetic drying oils typically comprise triglycerides comprising one mole of glycerine and three moles of an unsaturated fatty acid. The reactivity of the oils results from the presence of unsaturated fatty acid esters having two or more non-conjugated double bonds separated by a single methylene group:

combined with two or more other conjugated or non-conjugated double bonds. Typical compositions of some of the more important drying oils are shown in the following table.

TABLE 1

Typical Fatty Acid Composition of Drying Oils From Seeds, [a]%

| Oil | Saturated[b] | Oleic | Linoleic | Linolenic |
| --- | --- | --- | --- | --- |
| linseed | 10 | 22 | 16 | 52 |
| perilla | 7 | 14 | 16 | 63 |
| safflower | 10 | 13 | 77 | |
| soybean | 16 | 24 | 51 | 9 |
| sunflower[c] | 14 | 14 | 72 | |
| sunflower[c] | 9 | 72 | 19 | |
| tung[d] | 6 | 4 | | |
| walnut | 8 | 16 | 72 | |

[a]Proportions shown are approximate; actual compositions can vary greatly.
[b]Palmitic and stearic acids.
[c]Examples of the especially large variations in composition of available sunflower oils.
[d]Also 82% l-eleostearic acid.

Such drying oils can be derived from flax seed in the form of linseed oil, other drying oils can be obtained from soybean that can be modified into a useful drying oil. Further, perilla, safflower, sunflower and walnut oil have limited use as drying oils but can be improved.

Such oils can be converted or modified into a drying oil by heating with catalytic materials that can yield a polyunsaturated material. Such oils are classified as drying oils through their capacity to form a solid film upon oxidative exposure to air. Semi-drying oils come up on exposure to air can form tacky, sticky or semi-solid films. Non-drying oils undergo substantially no change in viscosity upon exposure to oxidating conditions. Reactivity of drying oils typically relate to the number of methylene groups found between the double bonds in the molecule. The reactivity of these materials are well understood and form the basis of the reactivity of alkyd paints.

Still further, a stable detectable indicator of the presence of the antimastitis compositions of the invention can be obtained by incorporating a chemiluminescent materials in the composition. Chemiluminescence is the emission of light from chemical reactions at ordinary temperatures. Chemiluminescent reactions produce a reaction intermediate or a product in an electronically excited state. With radiated decay of the excited state, a quantum or quanta of light is produced resulting in the visible indication of the presence of the chemiluminescence system. When the excited state is a singlet, the radiative process is fluorescent, when the excited state is a triplet, phosphorescent emission is obtained. Electronically excited states can emit UV or infrared radiation as well as visible light, however, the visible chemiluminescence is preferred. Because of the oxidative nature of the chemilumnescent reaction, the peroxide generated chemiluminescence is a preferred mechanism. Chemiluminescence systems are selected such that the energy content of the 167 kJ-ein$^{-1}$ to 293 kJ-ein$^{-1}$ and an excited state where a visible light must have that same energy with respect to its ground state. The excitation energy requirement is generally met by the sum of total reaction enthalpy and activation energy. Excitation appears to be general for this reaction but yields of excited products vary substantially with the substituents on the cyclic form. In liquid phase, chemiluminescence, two carbonyl groups are often formed by simultaneous decomposition of an intermediate yielding an excited species, carbon dioxide and other by-products. The excited species is often the source of visible light. In such reactions, substantial heat of formation of the carbonyl groups meets the energy requirement for the excited species. Substances that can provide the reaction including 1,2-dioxetanes, alpha peroxy lactones (1,2-dioxetanes), peroxy oxalate, luminol (phthalhydrazide) and organo metallic compounds.

Preferred chemiluminescence systems including peroxy oxalate systems. In such systems, the excited species is activated through the reaction of hydrogen peroxide, a catalyst and an oxalate species. A proposed mechanism for such reaction is shown as follows:

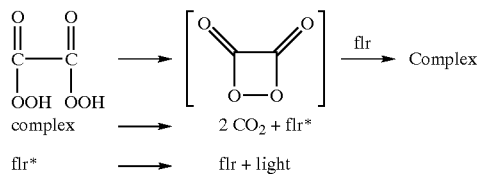

This system, peroxalate is converted to a dioxetanedione, a highly unstable intermediate which decomposes into carbon dioxide and an activated fluorescing species (flr*) that releases the visible light. Peroxy oxalate chemiluminescence is a very efficient non-enzymatic chemiluminescence. Quantum efficiencies approach 27% for oxalate esters prepared from 2,4,6-trichlorophenol, 2,4-dinitrophenol, and 3-trifluoromethyl-4-nitrophenol with fluorescers including rubrene or 5,12-bis(phenolethynyl)napthacene.

In the antimastitis compositions of the invention, we believe that the organic chemiluminescent species can be included in the acid part while the peroxide materials can be combined in the chlorite part or vice versa or maintain separately as a third oxidizing part (part 3). In use, part 1 containing the chemiluminescence species can be combined with part 2 containing the peroxide or the activating chlorite part or vice versa or optionally such parts can be combined with a third peroxide containing part. The luminescent species can be included in the acid part or vice versa in an amount of about 0.1 to 10 wt %, preferably, 0.5 to about 5 wt %. The peroxide material is included in a chlorite part or vice versa in an amount such that the final combined antimastitis composition contains from about 1 to about 10 wt % hydrogen peroxide. Hydrogen peroxide solutions that are stabilized and contain from about 5 to about 15 wt % hydrogen peroxide can be used since they tend to be relatively storage stable for a sufficient period of time for use in these compositions.

As discussed above, the present invention may generally comprise in a mastitis control and prevention treatment composition a carrier, an acid part, an acidulant or admixture, an antimicrobial agent or admixture, a rheology modifier or admixture, a film-forming agent or admixture, a buffer system, a hydrotrope or admixture, an emollient or admixture, a surfactant or surfactant admixture, a chromophore or colorant, and optional adjuvants. The preferred compositions of this invention comprise ingredients which are generally regarded as safe, and are not of themselves or in admixture incompatible with milk or milk by-products. Likewise, ingredients may be selected for any given composition which are cooperative in their combined effects whether incorporated for antimicrobial efficacy, physical integrity of the formulation or to facilitate healing and the health of the teat. Generally, the composition comprises a carrier which functions to dilute the active ingredients and facilitates application to the intended surface. The carrier is generally an aqueous medium such as water, or an organic liquid such as an oil, a surfactant, an alcohol, an ester, an ether, or an organic or aqueous mixture of any of these. Water is preferred as a carrier or diluent in compositions of this invention because of its universal availability and unquestionable economic advantages over other liquid diluents.

Acidulants are necessary ingredients within the mastitis control treatments of the invention to maintain the appropriate pH for dissociation of the chlorite/chlorine dioxide release agent and to prevent dissociation of heptanoic, octanoic, nonanoic, decanoic and undecanoic carboxylic acids employed as non-fugitive antimicrobial agents. Carboxylic acids become increasingly biocidal as the pH falls below their pK$_a$ value; consequently, for the carboxylic acids mentioned above, a pH ranging from about 2.5 to 5.5, preferably from about 2.5 to 4.5 and most preferably from about 2.5 to 3.5 is desirable. The acidic component used to prepare the acidic teat dip compositions of the invention will comprise a weak inorganic acid or a weak organic acid which can be dissolved in the aqueous system of the invention to produce an acidic pH. A pH substantially less than about 1 can result in substantial irritation, while a pH greater than about 5 can unacceptably reduce the efficiency of the composition. The term "weak" as used in reference to an acidic component is intended to refer to an acid in which the first dissociation step does not proceed essentially to completion when the acid is dissolved in water at ambient temperatures at a concentration within a range useful to form the present compositions. Such inorganic and organic acids are also referred to as weak electrolytes as the term is used in Textbook of Quantitative Inorganic Analysis, I. M. Kolthoff et al., eds., The Macmillan Co. (3d ed., 1952) at pages 34–37, the disclosure of which is incorporated by reference herein.

Most common commercially-available weak inorganic and organic acids can be used in the invention. Preferred weak inorganic acids include phosphoric acid and sulfamic acid. Useful weak organic acids include acetic acid, hydroxyacetic acid, citric acid, tartaric acid and the like. Acidulants found useful include organic and inorganic acids such as citric acid, lactic acid, acetic acid, glycolic acid, adipic acid, tartaric acid, succinic acid, propionic acid, malic acid, alkane sulfonic acids, cycloalkane sulfonic acids, as well as phosphoric acid and the like or mixtures thereof. Preferred acidulants are those commonly referred to as $C_{2-6}$ alpha-hydroxycarboxylic acids, that group of acids which contain a hydroxy function in the alpha position directly adjacent to the carbon atom bearing the carboxyl function, examples of alpha-hydroxymonocarboxylic acids being glycolic, lactic and hydroxybutanoic acid; and, examples of hydroxydicarboxylic acids being malic and tartaric acids. We have found a surprising interaction between the acidulant material and a second antimicrobial acid composition. Preferably, the acidulant material comprises the $C_{2-6}$ alpha-hydroxy carboxylic acid in combination with a secondary antimicrobial acid composition. The second antimicrobial acid composition can comprise a $C_{7-11}$ carboxylic acid or a hydrocarbon sulfonic acid composition. These materials work together to provide a cooperative antimicrobial action which effects initial kill from chlorine dioxide contributed by the acidulated chlorite and a long lasting kill in the barrier layer from the carboxylic acid/sulfonic acid material. This cooperation of ingredients is an important aspect of the invention.

Used in personal care products, alpha-hydroxycarboxylic acids absorb moisture from the atmosphere and therefore, when applied topically, increase moisture content and plasticity of the stratum corneum. They have had significant impact on skin treatment due to their ability to reduce corneocyte adhesion and accelerate cell proliferation within the basal layers. Though mechanism of action is not yet fully understood, alpha-hydroxycarboxylic also are thought to stimulate synthesis of collagen and mucopolysaccharides in the dermis. At use levels under 10%, skin care benefits are derived through a continued pattern of product usage. Continued use of products with alpha-hydroxycarboxylic acids levels below 10% has been shown to result in gradual reduction of fine lines and an improvement in skin texture through accelerated desquamation. Although conjecture at present, it is believed that some, if not all of these advantages may also be transferred upon the bovine teat skin. By incorporating an alpha-hydroxycarboxylic acid, healing may be accelerated; and, by "smoothing" the dermal surface, cleaning and asepsis may be improved. The most preferred alpha-hydroxycarboxylic acid for compositions of this invention is lactic acid.

Numerous inorganic and organic antimicrobial agents may be utilized in teat dip compositions including (but not limited to) chlorine and bromine release compounds (e.g. alkali and alkaline earth hypochlorites and hypobromites, isocyanurates, chlorinated derivatives of hydantoin, sulfamide, amine, etc.), iodine release complexes of surfactants or polymers such as polyvinylpyrrolidone (termed iodophors), quaternary ammonium compounds, chlorhexidine salts, peroxide and peroxyacid compounds, protonated short chain carboxylic acids, acidified anionic surfactants and chlorine dioxide. Of these typically applied antimicrobial agents which have been investigated for control of bovine mastitis, protonated short chain ($C_{7-11}$) carboxylic acids, acidified alkylaryl sulfonates and chlorine dioxide are proven efficacious against mastitis causing microorganisms; and, are preferred in compositions of the present invention. More specifically, dodecylbenzene sulfonic acid, protonated $C_{7-11}$ carboxylic acids and chlorine dioxide are especially preferred antimicrobial agents.

The composition of the invention may also contain one or more rheology modifiers, to enhance viscosity, or thicken and cause the aqueous treatment to cling to the surface skin of the teat. Clinging enables the composition to remain in contact with transient and resident pathogenic bacteria for longer periods of time, promoting microbiological efficacy and resisting waste because of excessive dripping. The rheology modifier may be a film former or act cooperatively with a film-forming agent to form a barrier that provides additional protection. Water soluble or water dispersible rheology modifiers that are useful can be classified as inorganic or organic. The organic thickeners can further be divided into natural and synthetic polymers with the latter still further subdivided into synthetic natural-based and synthetic petroleum-based.

Inorganic thickeners are generally compounds such as colloidal magnesium aluminum silicate (VEEGUM®), colloidal clays (Bentonites), or silicas (CAB-O-SILS®) which have been fumed or precipitated to create particles with large surface to size ratios. Natural hydrogel thickeners of use are primarily vegetable derived exudates. For example, tragacanth, karaya, and acacia gums; and extractives such as caragheenan, locust bean gum, guar gum and pectin; or, pure culture fermentation products such as xanthan gum are all potentially useful in the invention. Chemically, all of these materials are salts of complex anionic polysaccharides. Synthetic natural-based thickeners having application are cellulosic derivatives wherein the free hydroxyl groups on the linear anhydro-glucose polymers have been etherified or esterified to give a family of substances which dissolve in water and give viscous solutions. This group of materials includes the alkyl and hydroxyllalkycelluloses, specifically methylcellulose, hydroxyethylmethylcellulose, hydroxypropylmethylcellulose, hydroxybutylmethycellulose, hydroxyethylcellulose, ethylhydroxyethylcellulose, hydroxypropylcellulose, and carboxymethylcellulose. Synthetic petroleum-based water soluble polymers are prepared by direct polymerization of suitable monomers of which polyvinylpyrrolidone, polyvinylmethylether, polyacrylic acid and polymethacrylic acid, polyacrylamide, polyethylene oxide, and polyethyleneimine are representative.

All thickeners do not work with equal effectiveness in this invention. Preferred aqueous thickening agents which are more useful in this invention are those which are extremely pseudoplastic (non-Newtonian, rapid relaxation), tend not to develop a rigid three-dimensional structure from interpolymer interactions, have a low or negligible viscoelastic character and possess a high gel strength. Such rheological properties are manifested in a teat dip composition which has a smooth flowing appearance, is easy to pour and apply onto the teat, coats uniformly without forming mucilage streamers as the applicator is withdrawn and remains firmly in place without significant sag. Examples of preferred rheology modifiers are xanthan gum and the hydroxylalkylcelluloses. Generally, the concentration of thickener used in the present invention will be dictated by the final composition any by the method of teat application. Spraying or misting requires a lower composition viscosity for easy and effective application of treatment than dipping. Film-forming barrier dips typically require high apparent viscosity necessary to form thick coatings on teats which insures improved prophylactic effect.

For compositions of this invention designed to provide a barrier for prophylactic protection, additional film-forming agents are included which typically work in conjunction with thickeners. In fact, many of the aforementioned rheology modifiers are themselves film formers of greater or lesser effectiveness; however, a preferred grade of polyvinyl alcohol when used with preferred thickeners such as xanthan gum or hydroxyalkylcelluloses affords particularly useful properties to compositions of this teaching, most notably the development of "balanced" films on treated teats which are sufficiently water-sensitive to be stripped off with conventional udder washing, but capably adherent to the teat skin to withstand premature loss of integrity between milkings and intrinsically resistant to environmental exposure; and, in addition, are of such structure as to successfully occlude antimicrobial agents within the film matrix for continuing biocidal effect against mastitis causing organisms. The success of the barriers thus formed by compositions of this invention are, in part, a consequence of a hydrophobic-hydrophilic balance, caused when non-volatile ingredients, especially fatty acids, surfactants and hydrotropes, become resident throughout the film and whose individual properties become additive with those characteristics of the thickeners and film formers. Such inclusions also plasticize the film and render it pliable.

Polyvinyl alcohol compositions can be used as a film former. Variation of film flexibility, water sensitivity, ease of solvation, viscosity, film strength and adhesion can be varied by adjusting molecular weight and degree of hydrolysis. The preferred polyvinyl alcohol for use in compositions herein has a degree of hydrolysis greater than 92%, preferably greater than 98%, most preferably greater than 98.5%; and, has a molecular weight (Mn) that falls in the range of between about 15,000 and 100,000, but preferably between 40,000 and 70,000 corresponding to a solution viscosity (4% wt aqueous solution measured in centipoise (cP) at 20° C. by Hoeppler falling ball method) of 12–55 cP and 12–25 cP respectively.

The classical definition of a buffered solution is one containing both a weak acid and its conjugate weak base, whose pH changes only slightly on addition of acid or alkali. The weak acid becomes a buffer when alkali is added, and the weak base becomes a buffer when acid is added. Maintenance of the pH of compositions described in the present invention is necessary to minimize undesirable chemical changes which may inhibit the microbiological efficacy of the antimicrobial agent or cause toxic or irritating effect upon the teat. Any compatible organic or inorganic material or mixture of materials which has the desired effect of maintaining the composition pH within prescribed ranges can by utilized as the buffering agent or system in the instant invention. Of primary concern are pH shifts caused by naturally occurring chemicals brought into the composition, after application onto the teat, by skin exudations, milk or environmental soils; and, pH drifting which sometimes accompanies chemical equilibriums established within compositions as ingredients are changed or concentrations varied.

In general, the pH of bovine mastitis control treatments can vary from a low of about pH 2.0 to a maximum of approximately 11.0 depending primarily upon the choice of antimicrobial agent being incorporated in the composition because optimal efficacy normally occurs with a specific, narrow, pH range. Therefore the buffering agent or system is chosen accordingly. The preferred pH range of compositions of this invention is typically from 2.5 to 5.5 most preferably, about 2.5 to 3.5—the lower value being a limit to prevent excessive irritation on the teat surface; and, the upper limit set to enhance chlorine dioxide formation and maintain antimicrobial effect of the protonated carboxylic acid(s) and/or acidified anionic surfactant. A typical and preferred buffer system would be citric acid and its alkali metal salt. However, any acidulant and corresponding conjugate weak base could be used.

Solubilizing agents called hydrotropes or couplers may be generally used in compositions of the present invention to maintain physical single phase integrity and storage stability. To this end, any number of ingredients known to those skilled in formulation art may be employed, such as mono-functional and polyfunctional alcohols. These preferably contain from about 1 to about 6 carbon atoms and from 1 to about 6 hydroxy groups. Examples include ethanol, isopropanol, n-propanol, 1,2-propanediol, 1,2-butanediol, 2-methyl-2,4-pentanediol, mannitol and glucose. Also useful are the higher glycols, polyglycols, polyoxides, glycol ethers and propylene glycol ethers. Additional useful hydrotropes include the free acids and alkali metal salts of sulfonated alkylaryls such as toluene, xylene, cumene and phenol or phenol ether or diphenyl ether sulfonates; alkyl and dialkyl naphthalene sulfonates and alkoxylated derivatives. The most preferred hydrotrope for the most preferred embodiments of this invention is 1-octane sulfonate or mixtures of 1-octane sulfonate and 1,2-octane disulfonate manufactured and held for proprietary use under the name NAS by Ecolab Inc, St. Paul, Minn.

Teat dip compositions of the present invention generally also comprise an emollient and/or humectant to lubricate, condition, soothe, smooth, soften, and generally reduce and promote the healing of irritation on the teat surface. Such irritation may result either from the antimicrobial agent, from the mechanical action of the milking machine or from environmental conditions such as wind chill, dehydration, abrasion and sunburn. Any water soluble or dispersible skin conditioning agent may be used in this present invention. Compositions such as polyhydric alcohols are useful in the invention including glycerin, sorbitol, mannitol, and propylene glycol and its homopolymers; fatty acid esters of simple monohydril alcohols including isopropyl palmitate or isopropyl myristate and similar esters; polyol esters of fatty acids; and, ethoxylated lanolins, vegetable oils, and similar natural sourced derivatives such as aloe. Preferred emollients to be used in the invention include glycerin, sorbitol, and propylene glycol. A preferred emollient system for use in the invention comprises a combination of lanolin and a polyhydroxy emollient composition. The preferred emollient composition comprises lanolin, a lanolin derivative combined with a polyhydroxy compound selected from the group consisting of glycerin, sorbitol, glucitol, propylene glycol and mixtures thereof. Lanolin, a commodity material, also known as wool fat, oespios, agnin, alaporin, is a waxy fatty secretion of sheep. In sheep, sebaceous glands secrete a "fat-like" waxy secretion which is deposited onto the wool fiber. Chemically a wax, the material is a complex mixture of esters and polyesters of 33 high-molecular-weight alcohols and 33 fatty acids. The alcohols are of three types: aliphatic alcohols, steroidal alcohols and triterpenoid alcohols; the acids are of three types: saturated non-hydroxylated acids, unsaturated non-hydroxylated acids and hydroxlyated acids. Liquid lanolin is rich in low molecular weight branched aliphatic acids and alcohols while waxy lanolin is rich in high molecular weight straight chain acids and alcohols. Reviews regarding compositions, derivatives, modifications and uses are found in *Barnet, Drug and Cosmet. Ind.*, Ad, 744 (1957); 83, 292 (1958); Leideritz, *Chem. Ikerztg.*, 83, 707 (1959); F. Fawaz et al., *Ann. Pharm. Franc.*, 33, 217, 226 (1973). Rheological properties of lanolin are discussed in F. Poisieux, *Pharm. Acta. Helv.*, 51, 289 (1976). Please also the monograph: E. V. Truter, *Wool Wax, Chemistry and Technology*, (Interscience, 1956). The typical lanolin product contains about 20–25 wt % water and is yellowish white in color having a slight odor. The material is, for all practical purposes, insoluble in water but is soluble in chloroform or ether with the inherent separation of water from the wax lipid mass. Anhydrous lanolin is yellowish, tenacious, semisolid fatty appearing material, with a slight odor. Anhydrous lanolin melts at 38–42° C., is insoluble in water, but sparingly soluble in alcohol while freely soluble in benzene, chloroform, ether, carbon disulfide, acetone or petroleum ether. Lanolin is a natural product material produced in the manufacture of wool yarn. A preferred emollient composition contains a lanolin derivative in combination with a polyhydroxy compound. A variety of relatively neutral emollient lanolin species are known including a lanolin glycerol ester or ether, acetylated lanolin alcohol, lanolinamide DEA isopropyl lanolate, oleyl lanolate, hydrogenated lanolin, hydroxylated lanolin, lanolin lanoleate, isobutylated lanolin oil, lanolin ricinoleate, lanolin wax and a polyethylene glycol derivative of lanolin (PEG-lanolin). The PEG-lanolin derivative (CAS number 61790-81-6) can contain from about 5 to about 100 moles of ethylene glycol per mole of the PEG lanolin derivative. Preferred derivatives comprise about 40 to 85 moles of ethylene oxide per mole derivative. These materials are sold under the tradenames LANETO-50; SOLAN-50; ETHOXYLAN-50; SOLULAN-75 from a variety of commercial sources. A preferred humectant for use in these materials comprises combining, in a fully formulated teat dip material, about 0.01 to about 100 parts by weight of the PEG lanolin derivative for each one part by weight of a polyhydroxy compound selected from the group consisting of glycerine, sorbitol, glucitol and mixtures thereof. The preferred teat dip compositions contain about 0.1 to about 15 wt % of the polyhydroxy humectant combination, preferably about 0.2 to 5 wt % and about 0.1 to 10 wt. %, preferably 0.5 to 5 wt. % of the lanolin composition. The combination of the lanolin derivative and the polyhydroxy emollient compound provides surprisingly enhanced soothing protection for animals exposed to repeated milking and harsh conditions.

The surfactant or surfactant admixture of the present invention can be selected from compatible water soluble or water dispersible nonionic, or anionic surface-active agents; or mixtures of each or both types. Nonionic and anionic surfactants offer diverse and comprehensive commercial selection, low price; and, most important, excellent detersive effect—meaning surface wetting. Surface-active or "wetting agents" function to increase the penetrant activity of the invention into the tissue surface at risk from mastitis causing pathogens. Nonionic surfactants useful in the invention are generally characterized by the presence of an organic hydrophobic group and an organic hydrophilic group and are typically produced by the condensation of an organic aliphatic, alkyl aromatic or polyoxyalkylene hydrophobic compound with a hydrophilic alkaline oxide moiety which in common practice is ethylene oxide or a polyhydration product thereof, polyethylene glycol. Practically any hydrophobic compound having a hydroxyl, carboxyl, amino, or amido group with a reactive hydrogen atom can be condensed with ethylene oxide, or its polydration adducts, or its mixtures with alkoxylenes such as propylene oxide to form a nonionic surface-active agent. The length of the hydrophilic polyoxyalkylene moiety which is condensed with any particular hydrophobic compound can be readily adjusted to yield a water dispersible or water soluble compound having the desired degree of balance between hydrophilic and hydrophobic properties.

Useful nonionic surfactants in the present invention include: Block polyoxypropylene-polyoxyethylene polymeric compounds based upon propylene glycol, ethylene glycol, glycerol, trimethylolpropane, and ethylenediamine as the initiator reactive hydrogen compound. Examples of polymeric compounds made from a sequential propoxylation and ethoxylation of initiator are commercially available under the trade name PLURONIC® manufactured by BASF Corp. PLURONIC® compounds are difunctional (two reactive hydrogens) compounds formed by condensing ethylene oxide with a hydrophobic base formed by the addition of propylene oxide to two hydroxyl groups of propylene glycol. This hydrophobic portion of the molecule weighs from about 1,000 to about 4,000. Ethylene oxide is then added to sandwich this hydrophobe between hydrophilic groups, controlled by length to constitute from about 10% by weight to about 80% by weight of the final molecule. TETRONIC® compounds are tetra-functional block copolymers derived from the sequential additional of propylene oxide and ethylene oxide to ethylenediamine. The molecular weight of the propylene oxide hydrotype ranges from about 500 to about 7,000; and, the hydrophile, ethylene oxide, is added to constitute from about 10% by weight to about 80% by weight of the molecule.

Also useful nonionic surfactants include the condensation products of one mole of alkyl phenol wherein the alkyl constituent, contains from about 8 to about 18 carbon atoms with from about 3 to about 50 moles of ethylene oxide. The alkyl group can, for example, be represented by diisobutylene, di-amyl, polymerized propylene, isoctyl, nonyl, and di-nonyl. Examples of commercial compounds of this chemistry are available on the market under the trade name IGEPAL® manufactured by Rhone-Poulenc and TRITON® manufactured by Union Carbide.

Likewise useful nonionic surfactants include condensation products of one mole of a saturated or unsaturated, straight or branched chain alcohol having from about 6 to about 24 carbon atoms with from about 3 to about 50 moles of ethylene oxide. The alcohol moiety can consist of mixtures of alcohols in the above delineated carbon range or it can consist of an alcohol having a specific number of carbon atoms within this range. Examples of like commercial surfactant are available under the trade name NEODOL® manufactured by Shell Chemical Co. and ALFONIC® manufactured by Vista Chemical Co.

Condensation products of one mole of saturated or unsaturated, straight or branched chain carboxylic acid having from about 8 to about 18 carbon atoms with from about 6 to about 50 moles of ethylene oxide. The acid moiety can consist of mixtures of acids in the above delineated carbon atoms range or it can consist of an acid having a specific number of carbon atoms within the range. Examples of commercial compounds of this chemistry are available on the market under the trade name NOPALCOL® manufactured by Henkel Corporation and LIPOPEG® manufactured by Lipo Chemicals, Inc. In addition to ethoxylated carboxylic acids, commonly called polyethylene glycol esters, other alkanoic acid esters formed by reaction with glycerides, glycerin, and polyhydric (saccharide or sorbitan/sorbitol) alcohols have application in this invention. All of these ester moieties have one or more reactive hydrogen sites on their molecule which can undergo further acylation or ethylene oxide (alkoxide) addition to control the hydrophilicity of these substances.

Other useful surfactants are nonionics made by adding ethylene oxide to ethylene glycol to provide a hydrophile of designated molecular weight; and, then adding propylene oxide to obtain hydrophobic blocks on the outside (ends) of the molecule. The hydrophobic portion of the molecule weighs from about 1,000 to about 3,100 with the central hydrophile comprising 10% by weight to about 80% by weight of the final molecule. These "reverse" PLURONIC®'s are manufactured by the BASF Corporation under the trade name PLURONIC® surfactants. Likewise, the TETRONIC® surfactants are produced by the BASF Corporation by the sequential addition of ethylene oxide and propylene oxide to ethylenediamine. The hydrophobic portion of the molecule weighs from about 2,100 to about 6,700 with the central hydrophile comprising 10% by weight to 80% by weight of the final molecule.

Tertiary amine oxides corresponding to the general formula:

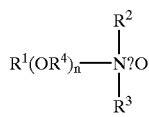

can be used wherein the ? bond is a conventional representation of a semi-polar bond; and $R^1$, $R^2$, and $R^3$ may be aliphatic, aromatic, heterocyclic, alicyclic groups or a combination of such groups thereof. Generally, for amine oxides of detergent interest, $R^1$ is an alkyl radical of from about 8 to about 24 carbon atoms; $R^2$ and $R^3$ are selected from the group consisting of alkyl or hydroxyalkyl of 1–3 carbon atoms and mixtures thereof; $R^4$ is an alkylene or a hydroxyalkylene group containing 2 to 3 carbon atoms; and n ranges from 0 to about 20. Useful water soluble amine oxide surfactants are selected from the coconut or tallow dimethyl amine oxides.

Also useful in the present invention are surface active substances which are categorized as anionics because the charge on the hydrophobe is negative; or surfactants in which the hydrophobic section of the molecule carries no charge unless the pH is elevated to neutrality or above (e.g. carboxylic acids). Carboxylate, sulfonate, sulfate and phosphate are the polar (hydrophilic) solubilizing groups found in anionic surfactants. Of the cations (counterions) associated with these polar groups, sodium, lithium and potassium impart water solubility and are most preferred in compositions of the present invention. Examples of suitable synthetic, water soluble anionic compounds are the alkali metal (such as sodium, lithium and potassium) salts or the alkyl mononuclear aromatic sulfonates such as the alkyl benzene sulfonates containing from about 5 to about 18 carbon atoms in the alkyl group in a straight or branched chain, e.g., the salts of alkyl benzene sulfonates or of alkyl naphthalene sulfonate, dialkyl naphthalene sulfonate and alkoxylated derivatives. Other anionic detergents are the olefin sulfonates, including long chain alkene sulfonates, long chain hydroxyalkane sulfonates or mixtures of alkenesulfonates and hydroxyalkanae-sulfonates and alkylpoly (ethyleneoxy) ether sulfonates. Also included are the alkyl sulfates, alkyl poly (ethyleneoxy) ether sulfates and aromatic poly (ethyleneoxy) sulfates such as the sulfates or condensation products of ethylene oxide and nonyl phenol (usually having 1 to 6 oxyethylene groups per molecule).

Complexed iodines offer the advantage of being chromophoric, i.e. easily visible when applied onto the teat. Other antimicrobial agents do not have this feature; therefore, compositions of this invention may include a water soluble or dispersible coloring agent (dye or pigment or mixtures) which renders the composition chromophoric, having sharp contrast to teat skin and permitting the dairy herd manager to visually discern that the teats have been treated.

Alternatively, the compositions of the invention may be comprised of any number of optional ingredients, i.e. adjuvants. Depending upon the benefits provided, adjuvants may partially or wholly displace the carrier in the composition. Generally, in accordance with the invention, there may be included within this composition formulary adjuvants which assist in the application of the invention with respect to physical and chemical stability, barrier film formation, teat health maintenance, performance, physical form and manufacturing process anesthetics. Of course, these functions may be accomplished exclusively by composition ingredients already described or admixtures thereof; however, formulary or application or performance situations may occur requiring additional effect which may be accomplished by introducing an additional inorganic or organic agent or agents and mixtures thereof into the composition.

The compositions of the invention may optionally include medicaments, for example sunscreens such as paramino benzoic acid and healing agents such as allantoin or urea to provide curative action and stimulation of formation of new tissue; preservatives such as methyl paraben, propyl paraben, sorbic and benzoic acids or salts thereof to retard bacterial growth and prolong shelf life; antioxidants such as BHT (butylated hydroxytoluene), BHA (butylated hydroxyanisole), TBHQ (tert-butylhydroquinone), or propyl gallate to retard oxidative or hydrolytic degradation; sequestering agents such as aminopolyacetates, polyphosphonates, aminpolyphosphonates, polycarboxylates, and condensed phosphates; dispersants or suspending agents having polyelectrolytic character such as polyacrylate and similar polycarboxylates of homopolymeric or copolymeric structure; and manufacturing processing agents, for example defoam additives employed to facilitate blending and mixing.

A wide variety of ingredients useful in mastitis control treatment can be included in the compositions hereof. This list is not intended to be exhaustive and other optional ingredients, which may not be listed, but which are well known in the art, may also be utilized in the composition. The examples are not intended to be limited in any way. In certain cases, some of the individual adjuvants may overlap other categories. The adjuvants employed will be selected so as not to interfere with the antimicrobial action of the composition and to avoid physical or chemical instability of the product.

Table "Bovine Mastitis Treatment Admixture Compositions", below, provides guidelines for consistent concentrations in accordance with this invention.

| INGREDIENT | USEFUL AMOUNT (WT. %) | PREFERRED (WT. %) | MORE PREFERRED (WT. %) |
|---|---|---|---|
| CARRIER | 40.0–98.0 | 50.0–98.0 | 60.0–98.0 |
| BLEND OF ACIDULANT/ ANTI-MICROBIAL | 1.0–12.0 | 1.0–10.0 | 1.0–8.0 |
| RHEOLOGY MODIFIER | 0.0–10.0 | 0.01–7.5 | 0.1–5.0 |
| FILM FORMER | 0.0–12.0 | 0.01–8.0 | 0.1–4.0 |
| BUFFER | 0.0–15.0 | 0.01–10.0 | 0.1–5.0 |
| HYDROTROPE | 0.0–20.0 | 0.0–15.0 | 0.1–10.0 |
| EMOLLIENT | 0.5–60.0 | 1.0–40.0 | 1.5–20.0 |
| SURFACTANT | 0.0–60.0 | 0.01–40.0 | 0.1–20.0 |
| INDICATOR/ COLORANT | 0.0–1.0 | 0.001–0.8 | 0.002–0.6 |
| UREA | 0.01–10 | 0.1–5 | 0.2–4 |
| OPTIONAL ADJUVANT | 0.0–5.0 | 0.1–4.0 | 0.1–30 |

The following examples and data are provided to illustrate preferred embodiments of the invention and contain a best mode.

EXAMPLE I

Example I is a representative embodiment of this invention which illustrates a bovine mastitis treatment having barrier film properties. Antimicrobial effect is provided by generation of chlorine dioxide caused by disproportionation of chlorite ion upon admixture of composition base with activator and by the resident biocidal activity of protonated nonanoic acid.

A 16 liter batch of the following experimental base formula part and 1 kilogram of the $ClO_2^{-1}$ part was prepared by blending the ingredients as shown.

Base Formula (Part I) (pH=2.8)

| Ingredients | Wt % | Grams |
|---|---|---|
| Glycerin, 96% | 5.00 | 800.05 |
| Isopropanol, 99% | 2.00 | 320.05 |
| Nonanoic (Pelargonic) Acid | 1.50 | 240.05 |
| Lactic Acid, 88% | 2.95 | 472.03 |
| *Xanthan Gum (KELTROL ® K5C151) | 0.30 | 48.02 |
| Deionized Water | 60.76 | 9721.62 |
| Potassium Benzoate | 0.20 | 32.01 |
| KOH, 45% | 0.29 | 46.40 |
| Octane Sulfonate | 17.00 | 2720.02 |
| **ELVANOL ® Premix, 10% | 10.00 | 1600.00 |
| TOTAL | 100.00 | 16000.25 |

*KELTROL ® K5C151 is a grade of xanthan gum manufactured by Kelco.
**ELVANOL ® Premix: 10% aqueous solution of ELVANOL ® 90-50. ELVANOL ® 90-50 is a grade of polyvinyl alcohol manufactured by E. I. duPont.

Activator $ClO_2^{-1}$ Formula (Part II) (pH=12.3):

| Ingredients | Wt % | Grams |
|---|---|---|
| Deionized Water | 50.00 | 500.00 |
| Sodium Chlorite, 25% | 50.00 | 500.00 |
| TOTAL | 100.00 | 1000.00 |

About 3376 grams of the base formula part were blended with about 92.89 grams of the $ClO_2^{-1}$ part (the $ClO_2^{-1}$ is 0.32% of total composition). The viscosity (Brookfield Model DV-II Viscometer, spindle No. 1, 20 rpms at 25° C.) was about 304 cps.

EXAMPLE II

Example II is a further example of this invention which differs from Example I in that the resident biocidal activity is contributed by dodecylbenzene sulfonic acid. The hydrotropic agent, octane sulfonate, is not required in this formula for physical stability.

A seven kilogram batch of the following base formula part and a one kilogram batch of the $ClO_2^{-1}$ activator part was prepared.

Base Formula (Part II) (pH=2.9)

| Ingredients | % | Grams |
|---|---|---|
| Glycerin, 96% | 5.00 | 350.10 |
| Dodecylbenzene Sulfonic Acid, 97% | 2.00 | 140.01 |
| Xanthan Gum *KELTROL ® K5C151 | 0.30 | 21.01 |
| Deionized Water | 78.14 | 5469.90 |
| Lactic Acid, 88% | 2.95 | 206.51 |
| KOH, 45% | 1.41 | 98.73 |
| Potassium Benzoate | 0.20 | 14.00 |
| **ELVANOL ® Premix, 10% | 10.00 | 700.06 |
| TOTAL | 100.00 | 7000.32 |

*KELTROL ® K5C151 is a grade of xanthan gum manufactured by Kelco.
**ELVANOL ®* Premix: 10% aqueous solution of ELVANOL ® 90-50. ELVANOL ® 90-50 is a grade of polyvinyl alcohol manufactured by E. I. duPont.

Activator $ClO_2^{-1}$ Formula (Part II) (pH=12.3)

| Ingredients | % | Grams |
|---|---|---|
| Deionized Water | 50.00 | 500.00 |
| Sodium Chlorite, 25% | 50.00 | 500.00 |
| TOTAL | 100.00 | 1000.00 |

About 3376 grams of the base formula part were mixed with about 92.98 grams of the $ClO_2^{-1}$ activator part. The stable rheology and pH of the combined formula is shown as follows:

| Viscosity: | As Mixed | pH |
|---|---|---|
| | Brookfield (#1, 20 rpm @ 25° C.) | |
| Brookfield: initial | 290 cps | 3.08 |
| Brookfield: 1 week | 296 cps | 3.09 |
| Brookfield: 2 weeks | n/a | n/a |
| Brookfield: 3 weeks | 291 cps | 2.97 |
| Brookfield: 4 weeks | 294 cps | 3.10 |

EXAMPLE III

Example III is a representative composition of the invention illustrating a bovine mastitis treatment without a barrier film property and having no thickening nor film-forming agents. A surfactant, NEODOL® 25-9, is included for teat cleansing and surface wetting.

A two hundred gram batch of the following experimental base formula and a I kilogram batch of the $ClO_2^{-1}$ activator part was made.

Base Formula (Part I) (pH=2.7)

| Ingredients | Wt % | Grams |
|---|---|---|
| Glycerin, 96% | 5.00 | 10.0 |
| $C_{12-15}$ alcohol (9 mole) ethoxylate NEODOL* 25-9 | 0.50 | 1.00 |
| Pelargonic Acid | 0.50 | 1.00 |
| Lactic Acid, 88% | 2.95 | 5.90 |
| Deionized Water | 75.44 | 150.88 |
| Octane Sulfonate | 7.00 | 14.00 |
| KOH, 45% | 0.61 | 1.22 |
| Dye-F, D & C Green #3-1.0% aq. active | 4.00 | 8.00 |
| *Pigment, 5.0% | 4.00 | 8.00 |
| TOTAL | 100.00 | 200.00 |

*Pigment: PYLAKLOR ® Yellow LX-10192 and Permanent Green S-722 (50:50 blend) manufactured by Pylam Products Co. Inc.

Activator $ClO_2^{-1}$ Formula (Part II) (pH=12.3)

| Ingredients | Wt % | Grams |
|---|---|---|
| Deionized Water | 50.00 | 500.00 |
| Sodium Chlorite, 25% | 50.00 | 500.00 |
| TOTAL | 100.00 | 1000.00 |

About 200 grams of the base formula were mixed with about 5.5 grams of the $ClO_2^{-1}$ activator part. pH of final mixture is about 2.9.

EXAMPLE IV

Example IV is a further modification of Example III using sorbitol as an emollient in place of glycerin. A two hundred gram batch of the following experimental base formula and a 1 kilogram batch of the $ClO_2^{-1}$ activator part was made.

Base Formula (Part I) (pH=2.7)

| Ingredients | Wt % | Grams |
|---|---|---|
| Sorbitol, 70% | 1.00 | 2.00 |
| $C_{12-15}$ alcohol 9 mole ethoxylate NEODOL ® 25-9 | 0.50 | 1.00 |
| Pelargonic Acid | 0.50 | 1.00 |
| Lactic Acid, 88% | 2.95 | 5.90 |
| Deionized Water | 79.49 | 158.98 |
| Octane Sulfonate | 7.00 | 14.00 |
| KOH, 45% | 0.56 | 1.12 |
| Dye-F, D & C Green #3, 1.0% aqueous active | 4.00 | 8.00 |
| *Pigment, 5.0% | 4.00 | 8.00 |
| TOTAL | 100.00 | 200.00 |

*Pigment: PYLAKLOR ® Yellow LX-10192 and Permanent Green S-722 (50:50 blend) manufactured by Pylam Products Co. Inc.

Activator $ClO_2^{-1}$ Formula (Part II) (pH=12.3)

| Ingredients | Wt % | Grams |
|---|---|---|
| Deionized Water | 50.00 | 500.00 |
| Sodium Chlorite, 25% | 50.00 | 500.00 |
| TOTAL | 100.00 | 1000.00 |

About 200 grams of the base formula were mixed with about 5.5 grams of the $ClO_2^{-1}$ activator part. pH of final mixture is about 2.9.

EXAMPLE V

Example V is a further composition of the invention illustrating a bovine mastitis treatment without a barrier film property, again having no thickening nor film-forming agents and using phosphoric acid as the acidulant. A surfactant, NEODOL® 25-9, is included for teat cleansing and surface wetting. A two hundred gram batch of the following experimental base formula and a 1 kilogram batch of the $ClO_2^{-1}$ activator part was made.

Base Formula (Part I) (pH=2.7)

| Ingredients | % | Grams |
|---|---|---|
| Sorbitol, 70% | 1.00 | 2.00 |
| $C_{12-15}$ alcohol 9 mole ethoxylate - NEODOL ® 25-9 | 0.50 | 1.00 |
| Pelargonic Acid | 0.50 | 1.00 |
| Phosphoric Acid, 75% | 1.00 | 2.00 |
| Deionized Water | 81.32 | 162.64 |
| Octane Sulfonate | 7.00 | 14.00 |
| KOH, 45% | 0.68 | 1.36 |
| Dye-F, D & C Green #3, 1.0% | 4.00 | 8.00 |
| *Pigment 5.0% | 4.00 | 8.00 |
| TOTAL | 100.00 | 200.00 |

*Pigment: PYLAKLOR ® Yellow LX-10192 and Permanent Green S-722 (50:50 blend) manufactured by Pylam Products Co. Inc.

Activator $ClO_2^{-1}$ Formula (Part II) (pH=12.3)

| Ingredients | % | Grams |
|---|---|---|
| Deionized Water | 50.00 | 500.00 |
| Sodium Chlorite, 25% | 50.00 | 500.00 |
| TOTAL | 100.00 | 1000.00 |

About 200 grams of the base formula were mixed with about 5.5 grams of the $ClO_2^{-1}$ activator part. pH of final mixture is about 2.9.

EXAMPLE VI

Examples VI, VII and VIII are compositional variations of Example I which contain the homologous carboxylic acids octanoic, decanoic and a mixture thereof respectively.

A two hundred gram batch of the following experimental base formula and a 1 kilogram batch of the $ClO_2^{-1}$ activator part was prepared.

Base Formula (Part 1) (pH=2.7)

| Ingredients | Wt % | Grams |
|---|---|---|
| Glycerin, 96% | 5.00 | 10.05 |
| Isopropanol, 99% | 2.00 | 4.01 |
| Octanoic Acid | 1.50 | 3.02 |
| Lactic Acid, 88% | 2.95 | 5.90 |
| Xanthan Gum KELTROL ® K5C151 | 0.30 | 0.61 |
| Deionized Water | 60.93 | 121.90 |
| Potassium Benzoate | 0.20 | 0.40 |
| KOH, 40% | 0.12 | 0.25 |
| Octane Sulfonate | 17.00 | 34.02 |
| *ELVANOL ® Premix, 10% | 10.00 | 20.09 |
| TOTAL | 100.00 | 200.25 |

*ELVANOL ® Premix: See p. 27

Activator $ClO_2^{-1}$ Formula (Part 2) (pH=12.3)

| Ingredients | Wt % | Grams |
|---|---|---|
| Deionized Water | 50.00 | 500.00 |
| Sodium Chlorite, 25% | 50.00 | 500.00 |
| TOTAL | 100.00 | 1000.00 |

The mixed product made with 100 grams of Part 1 formula and 2.75 grams of Part 2 is buffered to pH 2.9.

EXAMPLE VII

A 200 gram batch of the following experimental base formula and a 1 kilogram batch of the $ClO_2^-$ activator part was prepared.

Base Formula (Part 1) (pH 2.6)

| Ingredients | Wt % | Grams |
|---|---|---|
| Glycerin, 96% | 5.00 | 10.05 |
| Isopropanol, 99% | 2.00 | 4.00 |
| Decanoic Acid | 1.50 | 3.03 |
| Lactic Acid, 88% | 2.95 | 5.90 |
| Xanthan Gum KELTROL ® K5Cl51 | 0.30 | 0.61 |
| Deionized Water | 60.93 | 121.93 |
| Potassium Benzoate | 0.20 | 0.40 |
| KOH, 40% | 0.12 | 0.25 |
| Octane Sulfonate | 17.00 | 34.10 |
| *ELVANOL ® Premix, 10% | 10.00 | 20.00 |
| TOTAL | 100.00 | 200.27 |

*ELVANOL ® Premix: See p. 27

Activator $ClO_2^{-1}$ Formula (Part 2)(pH=12.3)

| Ingredients | Wt % | Grams |
|---|---|---|
| Deionized Water | 50.00 | 500.00 |
| Sodium Chlorite, 25% | 50.00 | 500.00 |
| TOTAL | 100.00 | 1000.00 |

The mixed product made with 100 grams of the Base Part 1 Formula combined with 2.75 grams of the activator Part 2 $ClO_2^{-1}$ formula. The material is buffered to pH 2.9.

EXAMPLE VIII

A 200 gram batch of the following experimental base formula and a 1 kilogram batch of the $ClO_2^-$ activator part was prepared.

Base Formula (Part 1) (pH 2.7)

| Ingredients | Wt % | Grams |
|---|---|---|
| Glycerin, 96% | 5.00 | 10.04 |
| Isopropanol, 99% | 2.00 | 4.01 |
| *KORTAC1D ® - C8:C10 (3:1) | 1.50 | 3.03 |
| Lactic Acid, 88% | 2.95 | 5.90 |
| Xanthan Gum KELTROL ® K5C151 | 0.30 | 0.61 |
| Deionized Water | 60.93 | 121.90 |
| Potassium Benzoate | 0.20 | 0.40 |
| KOH, 40% | 0.12 | 0.24 |
| Octane Sulfonate | 17.00 | 34.04 |
| *ELVANOL ® Premix, 10% | 10.00 | 20.01 |
| TOTAL | 100.00 | 200.18 |

*KORTACID ®: 3:1 Octanoic/decanoic blend manufactured by Akzo Chemical.
*ELVANOL ® Premix: See p. 27

Activator $ClO_2^{-1}$ Formula (Part 2) (pH=12.3)

| Ingredients | Wt % | Grams |
|---|---|---|
| Deionized Water | 50.00 | 500.00 |
| Sodium Chlorite, 25% | 50.00 | 500.00 |
| TOTAL | 100.00 | 1000.00 |

The mixed product made using 100 grams of Part 1 and 2.75 grams of Part 2 is buffered to pH 2.9.

EXAMPLE IX

Example IX is an additional variation of Example I containing heptanoic acid and n-propanol in place of nonanoic and isopropanol respectively.

A 1000 gram batch of this experimental base formula was prepared; and, 1000 grams of the $ClO_2^-$ part was prepared by blending the ingredients as shown. Two typical admixtures of parts I and II were then prepared or illustrated.

Base Formula (Part I) (pH 2.8)

| Ingredients | Wt % | Grams |
|---|---|---|
| Glycerin, 96% | 5.00 | 50.00 |
| n-Propanol, 99% | 1.50 | 15.03 |
| Heptanoic Acid | 1.00 | 10.03 |
| Lactic Acid, 88% | 2.95 | 29.51 |
| KELTROL ® K5C151 | 0.30 | 3.02 |
| Deionized Water | 71.13 | 711.38 |
| Potassium Benzoate | 0.20 | 2.03 |
| KOH, 45% | 0.42 | 4.21 |
| Octane Sulfonate | 7.50 | 75.00 |
| ELVANOL ® Premix, 10% | 10.00 | 100.07 |
| TOTAL | 100.00 | 1000.28 |

Activator Formula (Part II) (pH 12.0)

| Ingredients | Wt % | Grams |
|---|---|---|
| Deionized Water | 75.0 | 750 |
| Sodium Chlorite, 25% | 25.0 | 250 |
| TOTAL | 100.00 | 1000.00 |

Typical Mix Ratios:

| Base (g) | Activator (g) |
|---|---|
| 100 | 2.754 (6.25% active) → 0.16% $NaClO_2$ |
| 3376 | 93 (6.28% active) → 0.16% $NaClO_2$ |

EXAMPLE X

A 500 gram batch of the following experimental base formula was prepared for preliminary testing. This example is similar to Example I with n-propanol and half of the $NaClO_2$ amount.

Base Formula (Part I) (pH=2.8)

| Ingredients | Wt % | Grams |
|---|---|---|
| Glycerin, 96% | 5.00 | 25.00 |
| n-Propanol, 99% | 1.50 | 7.50 |
| Pelargonic Acid | 1.50 | 7.50 |
| Lactic Acid, 88% | 2.95 | 14.75 |
| *KELTROL ® K5C151 | 0.30 | 1.50 |
| Deionized Water | 71.13 | 266.30 |
| Potassium Benzoate | 0.20 | 1.00 |
| KOH, 45% | 0.29 | 1.25 |
| Octane Sulfonate | 17.00 | 85.00 |
| *ELVANOL ® Premix, 10% | 10.00 | 50.00 |
| **Pigment | 8.00 | 40.00 |
| TOTAL | 100.00 | 500.00 |

*ELVANOL ® Premix: See p. 27
**Pigment: See p. 29

Activator Formula (Part II) (pH=12.0)

| Ingredients | Wt % | Grams |
|---|---|---|
| Deionized Water | 75.00 | 375.00 |
| Sodium Chlorite, 25% | 25.00 | 125.00 |
| TOTAL | 100.00 | 500.00 |

Typical Mix Ratios:

| Base (g) | Activator (g) |
|---|---|
| 3376 | 186 g (6.25% active) → 0.32% $NaClO_2$ |
| 3376 | 93 (6.28% active) → 0.16% $NaClO_2$ |

EXAMPLE XI

A 1000 gram batch of the following experimental base formula was prepared for testing. This composition is similar to Example III with NAS and thickener.

Base Formula (Part I) (pH 2.7)

| Ingredients | Wt % | Grams |
|---|---|---|
| Glycerin, 96% | 5.00 | 50.00 |
| NEODOL ® 25-9 | .50 | 5.00 |
| Pelargonic Acid | 0.50 | 5.00 |
| Lactic Acid, 88% | 2.95 | 29.50 |
| KELTROL ® K5C151 | 0.10 | 1.00 |
| Deionized Water | 79.45 | 794.50 |
| Octane Sulfonate | 7.00 | 70.00 |
| KOH, 45% | 0.50 | 5.00 |
| *Pigment 5.0% | 4.00 | 40.00 |
| TOTAL | 100.00 | 1000.00 → pH = ~2.70 |

*Pigment: See p. 29

Activator Formula (Part II) (pH=12.3)

| Ingredients | Wt % | Grams |
| --- | --- | --- |
| Deionized Water | 50.00 | 500.00 |
| Sodium Chlorite, 25% | 50.00 | 500.00 |
| TOTAL | 100.00 | 1000.00 |

Typical Mix Ratios:

| Base (g) | Activator (g) |
| --- | --- |
| 450 | 12.39 (12.5% active) → 0.32% NaClO$_2$ |
| 225 | 225 |

EXAMPLE XII

A 1000 gram batch of the following experimental base formula was prepared for testing. This composition is similar to Example IV with an octane sulfonate.

Base Formula (Part I) (pH 2.7)

| Ingredients | Wt % | Grams |
| --- | --- | --- |
| Sorbitol, 70% active | 1.00 | 10.00 |
| NEODOL ® 25-9 | 0.50 | 5.00 |
| Pelargonic Acid | 0.50 | 5.00 |
| Lactic Acid, 88% active | 2.95 | 29.50 |
| Deionized Water | 83.49 | 834.90 |
| Deionized Water | 79.45 | 794.50 |
| Octane sulfonate | 7.00 | 70.00 |
| KOH, 45% | 0.56 | 5.60 |
| *Pigment 5.0% | 4.00 | 40.00 |
| TOTAL | 100.00 | 1000.00 → pH = ~2.70 |

*Pigment: See p. 29

Activator Formula (Part II) (pH 12.3)

| Ingredients | Wt % | Grams |
| --- | --- | --- |
| Deionized Water | 50.00 | 500.00 |
| Sodium Chlorite, 25% active | 50.00 | 500.00 |
| TOTAL | 100.00 | 1000.00 |

Typical Mix Ratios

| Base (g) | Activator (g) |
| --- | --- |
| 450 | 12.39 (12.5% active) → 0.32% NaClO$_2$ |
| 225 | 225 |

EXAMPLE XIII

A 1500 gram batch of the following experimental base formula was prepared for testing. Similar to Example III with NAS, thickener and heptanoic acid.

Base Formula (Part I) (pH=2.7)

| Ingredients | Wt % | Grams |
| --- | --- | --- |
| Glycerin, 96% | 5.00 | 75.00 |
| NEODOL ® 25-9 | 0.50 | 7.50 |
| Heptanoic Acid | 0.50 | 7.50 |
| Lactic Acid, 88% | 2.95 | 44.25 |
| KELTROL ® K5C151 | 0.10 | 1.50 |
| Deionized Water | 80.45 | 1206.75 |
| NAS-FAL | 6.00 | 90.00 |
| KOH, 45% | 0.50 | 7.50 |
| Pigment 5.0% | 4.00 | 60.00 |
| TOTAL | 100.00 | 1500.00 |

Activator Formula (Part II) (pH 12.0)

| Ingredients | Wt % | Grams |
| --- | --- | --- |
| Deionized Water | 75.00 | 75.00 |
| Sodium Chlorite, 25% | 25.00 | 25.00 |
| TOTAL | 100.00 | 100.00 |

Typical Mix Ratios

| Base (g) | Activator (g) |
| --- | --- |
| 50 | 1.377 (6.25% active) |
| 100 | 2.754 (6.25% active) |
| 450 | 12.39 (6.25% active) |

EXAMPLE XIV

A 1500 gram batch of the following experimental base formula was prepared for testing. Similar to Example IV with NAS and heptanoic acid.

Base Formula (Part I) (pH 2.7)

| Ingredients | Wt % | Grams |
| --- | --- | --- |
| Sorbitol, 70% | 1.00 | 15.00 |
| NEODOL ® 25-9 | 0.50 | 7.50 |
| Heptanoic Acid | 0.50 | 7.50 |
| Lactic Acid, 88% | 2.95 | 44.50 |
| Deionized Water | 80.45 | 1206.75 |
| NAS-FAL | 6.00 | 90.00 |
| KOH, 45% | 0.54 | 8.10 |
| **Dye/Pigment 5.0% | 4.00 | 60.00 |
| TOTAL | 100.00 | 1500.00 |

** Pigment: See p. 29

Activator Formula (Part II) (pH=12.0)

| Ingredients | Wt % | Grams |
|---|---|---|
| Deionized Water | 75.00 | 75.0 |
| Sodium Chlorite, 25% | 25.00 | 25.0 |
| TOTAL | 100.00 | 100.00 |

Typical Mix Ratios

| Base (g) | Activator (g) |
|---|---|
| 50 | 1.377 (6.25% active) |
| 100 | 2.754 (6.25% active) |
| 450 | 12.39 (6.25% active) |

Germicidal and Detergent Sanitizing Action of Disinfectants Testing Created from AOAC Method 960.09

A test to determine the efficacy of antimicrobial products used for sanitizing precleaned, nonporous food contact surfaces.
Culture Media
1. Nutrient Agar A:
2. Nutrient Agar B (French Slants):
Subculture Media
1. Tryptone Glucose Extract Agar (TGE):
2. Neutralized Tryptone Glucose Extract Agar:
The neutralizer used should be appropriate for test substance inactivation.
Reagents
1. Neutralizer Stock:
   a. A mixture of 49.5 mL Chambers solution and 49.5 mL of 1% aqueous $Na_2S_2O_3$
2. Neutralizer Blanks:
   a. Aseptically dispense 9 ml of neutralizer into sterile 25×1 50 mm test tubes for use in the test.
3. Phosphate Buffer Stock (0.25M)
4. Phosphate Buffer Dilution Water
Apparatus
1. Glassware
   250 ml Erlenmeyer flasks, 100 ml volumetric flasks, pipettes, glass beads, 20×150 and 25×150 mm test tubes. Sterilize for 20 minutes at 121° C. or in a dry air oven at 180° C. for 180 minutes.
2. Petri Dishes
   Sterile disposable petri dishes, 15×100 mm.
3. French Bottles (milk dilution bottles)
   175 ml flint glass bottles
4. Water Bath
   Constant temperature water bath that can maintain a test temperature ±2° C. of required test temperature. Monitor temperature throughout the test.
5. Transfer Loops
   Suitable metal or plastic disposal transfer loops
6. Sterile Buchner Funnel Containing Whatman No. 2 Filter Paper

*Staphylococcus aureus* ATCC 6538
*Escherichia coli* ATCC 11229
Maintain on Nutrient Agar A slants at 4° C. with transfers to new stock slants once per month (reference SOP MS031 for culture maintenance). From the stock culture slant, make >3 and <30 consecutive transfers on nutrient agar slants with incubation at 37° C.±2° C. for 20–24 hours. If only one daily transfer has been missed, no special procedures are required; if 2 or more daily transfers are missed, repeat with 3 daily transfers.

Inoculate french slants by washing the growth from the Nutrient Agar A slant into 99 ml of phosphate buffer as follows: Use 5 ml of buffer on the slant and rinse this into the balance of the 99 ml of buffer. Mix this suspension well and add 2 ml of suspension to each french slant. Tilt the slant back and forth to cover the surface. Remove the excess suspension Aseptically. Incubate the slants at 37° C.±2° C. for 18–24 hours.

Remove the culture from the agar surface using 3 ml of phosphate buffer and sterile glass beads rotated back and forth to remove the growth. Filter the suspension through a sterile Buchner funnel containing Whatman No. 2 filter paper that has been prewet with 1 ml of phosphate buffer. Collect the suspension in a sterile test tube.

Standardize the culture suspension by dilution using sterile phosphate buffered water to yield $10 \times 10^9$ organisms per milliliter. $10 \times 10^9$ organisms/ml corresponds roughly to % transmittance readings of 0.1% to 1.0%T at 580 nm. It is recommended that each individual operator determine what %T readings they need to achieve a $10 \times 10^9$ organisms/ml culture suspension prior to performing this test since validity of the test is based on having the proper inoculum.

Operating Technique
Dispense 99 ml of test substance into a sterile 250 ml Erlenmeyer flask. Prepare triplicate flasks for each test substance to be tested. Place flasks containing test substance into a 25° C. temperature water and let rest >20 minutes or until reaches test temperature.

Operating Technique with Milk Challange
Dispense 90 ml of test substance and 10 mL of milk challange into a sterile 250 ml Erlenmeyer flask, mix and remove 11.0 mL. Prepare duplicate flasks for each test substance to be tested. Place flasks containing test substance into a 25° C. temperature water and let rest >20 minutes or until reaches test temperature Enumerate inoculum numbers in sterile phosphate buffer. Enumeration of inoculum numbers will be performed as follows:

| Prepared Test Culture | 1:100 $\rightarrow 10^0$ | 1:100 $\rightarrow 10^{-2}$ | 1:100 $\rightarrow 10^{-4}$ | 1:100 $\rightarrow 10^{-6}$ |
|---|---|---|---|---|

From the $10^{-6}$ dilution, plate 1 ml ($10^6$) and 0.1 ml ($10^{-7}$) in quadruplicate. Use pour plate technique with TGE medium. Invert and incubate at 37° C.±2° C. for 48 hours. Whirl the test flasks and add 1 ml of culture to 99 ml of the test substance dilution midway between the side of the flask and the center. Avoid touching the sides of the flask with the pipette. Transfer 1 ml portions to the appropriate neutralizer (based on inactivation of the test substance) after 15 seconds exposure and mix well. Longer exposure times may be used depending on the test substance, previous testing and/or the study.

For regulatory documentation testing, plate 1 ml ($10^{-1}$) and 0.1 ml ($10^{-2}$) from the neutralizer blank tube in quadruplicate. For non-regulatory testing, serial dilutions may be performed in sterile phosphate buffer to yield dilutions of $10^{-1}$, $10^{-3}$, and $10^{-5}$. These dilutions are usually single platings. Use pour plate technique with neutralized (appropriate for test substance inactivation) TGE medium. Invert and incubate at 37° C.±2° C. for 48 hours.

Controls

1. Phenol Resistance Method

Determine the resistance of the test system to phenol according to standard procedures. The test system must meet the resistance specified in that SOP.

2. Neutralization Method (created from ASTM E 1054-91)

Duplicate neutralization method check(s) should be performed on each test system. If more than one use-solution concentration is used, test the most concentrate solution. Testing should be performed as follows:

Test A=Add 1 ml of test substance use-solution to 9 ml of the neutralizer and mix. Add 0.1 ml of ~$10^{-3}$ cfu/ml test system suspension, mix.

Test B=Add 1 ml of test substance diluent to 9 ml of the neutralizer and mix. Add 0.1 ml of ~$10^{-3}$ cfu/ml test system suspension, mix.

Test C=Add 0.1 ml of ~$10^{-3}$ cfu/ml test system suspension to 9 ml of phosphate buffered dilution water and mix.

Let tests stand for 30 minutes, then enumerate by plating 0.1 and 1 ml using pour plate technique and incubating 48 hours at est system specific temperature.

The data obtained will show the neutralizer to be effective if a≅c. The neutralizer will be observed not be detrimental to the cells if b≅c.

3. Diluent Control

Plate 1 ml of diluent used in the test. Incubate at 37° C.±2° C. for 48 hours.

TABLE 1

Zero Time Results

| Test Substance | Organic Challenge | Time Exposure | Log Reduction |
|---|---|---|---|
| *Escherichia coli* ATCC 11229 | | | |
| Ex. II Prepared (Jun. 19, 1997) | No Challenge | 15 seconds | 6.38 |
| Ex. II Prepared (Jun. 19, 1997) | 10% Milk | 15 seconds | 6.38 |
| UDDER GOLD PLUS Prepared (Jun. 19, 1997) | No Challenge | 15 seconds | 6.38 |
| UDDER GOLD PLUS Prepared (Jun. 19, 1997) | 10% Milk | 15 seconds | 6.38 |
| *Staphylococcus aureus* ATCC 6538 | | | |
| Ex. II Prepared (Jun. 19, 1997) | No Challenge | 15 seconds | 5.87 |
| Ex. II Prepared (Jun. 19, 1997) | 10% Milk | 15 seconds | 5.87 |
| UDDER GOLD PLUS Prepared (Jun. 19, 1997) | No Challenge | 15 seconds | 5.87 |
| UDDER GOLD PLUS Prepared (Jun. 19, 1997) | 10% Milk | 15 seconds | 5.87 |

Conclusions:

When freshly prepared both the composition of Example II and UDDER GOLD PLUS achieved a greater than 5 log reduction after 15 seconds with and without a 10% milk challenge against both *Staphylococcus aureus* ATCC 6538 and *Escherichia coli* ATCC 11229.

One Week Results

| Test Substance | Organic Challenge | Time Exposure | Log Reduction |
|---|---|---|---|
| *Escherichia coli* ATCC 11229 | | | |
| Ex. II Prepared (Jun. 19, 1997) | No Challenge | 15 seconds | 5.93 |
| Ex. II Prepared (Jun. 19, 1997) | 10% Milk | 15 seconds | 5.93 |
| UDDER GOLD PLUS Prepared (Jun. 19, 1997) | No Challenge | 15 seconds | 1.42 |
| UDDER GOLD PLUS Prepared (Jun. 19, 1997) | 10% Milk | 15 seconds | 0.61 |
| *Staphylococcus aureus* ATCC 6538 | | | |
| Ex. II Prepared (Jun. 19, 1997) | No Challenge | 15 seconds | 5.82 |
| Ex. II Prepared (Jun. 19, 1997) | 10% Milk | 15 seconds | 5.82 |
| UDDER GOLD PLUS Prepared (Jun. 19, 1997) | No Challenge | 15 seconds | 1.40 |
| UDDER GOLD PLUS Prepared (Jun. 19, 1997) | 10% Milk | 15 seconds | 0.59 |

After one week, Example II achieved a >5 log reduction after 15 seconds with and without a 10% milk challenge against both *Staphylococcus aureus* ATCC 6538 and *Escherichia coli* ATCC 11229. UDDER GOLD PLUS achieved a 1.42 log reduction against *Escherichia coli* ATCC 11229 in 15 seconds without milk, while achieving a 0.61 log reduction with the 10% milk challenge. Against *Staphylococcus aureus* ATCC 6538 UDDER GOLD PLUS achieved a log reduction of 1.42 without milk, and 0.59 with a 10% milk challenge.

Two Weeks Results

| Test Substance | Organic Challenge | Time Exposure | Log Reduction |
|---|---|---|---|
| *Escherichia coli* ATCC 11229 | | | |
| Ex. II Prepared (Jun. 19, 1997) | No Challenge | 15 seconds | 5.74 |
| Ex. II Prepared (Jun. 19, 1997) | 10% Milk | 15 seconds | 4.00 |
| UDDER GOLD PLUS Prepared (Jun. 19, 1997) | No Challenge | 15 seconds | 2.06 |
| UDDER GOLD PLUS Prepared (Jun. 19, 1997) | 10% Milk | 15 seconds | 0.26 |
| *Staphylococcus aureus* ATCC 6538 | | | |
| Ex. II Prepared (Jun. 19, 1997) | No Challenge | 15 seconds | 5.75 |
| Ex. II Prepared (Jun. 19, 1997) | 10% Milk | 15 seconds | 5.75 |
| UDDER GOLD PLUS Prepared (Jun. 19, 1997) | No Challenge | 15 seconds | 2.09 |
| UDDER GOLD PLUS Prepared (Jun. 19, 1997) | 10% Milk | 15 seconds | 0.32 |

After two weeks, Example II achieved a >5 log reduction after 15 seconds with and without a 10% milk challenge against *Staphylococcus aureus* ATCC 6538. Against *Escherichia coli* ATCC 11229 a reduction of 4.00 was seen with the 10% milk challenge while a 5.74 log reduction was seen without the challenge. UDDER GOLD PLUS achieved a 2.06 log reduction against *Escherichia coli* ATCC 11229 in 15 seconds without milk, while achieving a 0.26 log reduction with the 10% milk challenge. Against *Staphylococcus aureus* ATCC 6538 UDDER GOLD PLUS achieved a log reduction of 2.09 without milk, and 0.32 with a 10% milk challenge.

| Test Substance | Organic Challenge | Time Exposure | Log Reduction |
|---|---|---|---|
| Three Weeks Results | | | |
| *Escherichia coli* ATCC 11229 | | | |
| Ex. II Prepared (Jun. 19, 1997) | No Challenge | 15 seconds | 5.67 |
| Ex. II Prepared (Jun. 19, 1997) | 10% Milk | 15 seconds | 3.91 |
| UDDER GOLD PLUS Prepared (Jun. 19, 1997) | No Challenge | 15 seconds | 1.86 |
| UDDER GOLD PLUS Prepared (Jun. 19, 1997) | 10% Milk | 15 seconds | 0.26 |
| *Staphylococcus aureus* ATCC 6538 | | | |
| Ex. II Prepared (Jun. 19, 1997) | No Challenge | 15 seconds | 5.76 |
| Ex. II Prepared (Jun. 19, 1997) | 10% Milk | 15 seconds | 5.76 |
| UDDER GOLD PLUS Prepared (Jun. 19, 1997) | No Challenge | 15 seconds | 1.78 |
| UDDER GOLD PLUS Prepared (Jun. 19, 1997) | 10% Milk | 15 seconds | 0.36 |

After three weeks, Example II achieved a >5 log reduction after 15 seconds with and without a 10% milk challenge against *Staphylococcus aureus* ATCC 6538. Against *Escherichia coli* ATCC 11229 a reduction of 3.91 was seen with the 10% milk challenge while a 5.67 log reduction was seen without the challenge. UDDER GOLD PLUS achieved a 1.86 log reduction against *Escherichia coli* ATCC 11229 in 15 seconds without milk, while achieving a 0.26 log reduction with the 10% milk challenge. Against *Staphylococcus aureus* ATCC 6538 UDDER GOLD PLUS achieved a log reduction of 1.78 without milk, and 0.36 with a 10% milk challenge.

| Test Substance | Organic Challenge | Time Exposure | Log Reduction |
|---|---|---|---|
| Four Weeks Results | | | |
| *Escherichia coli* ATCC 11229 | | | |
| Ex. II Prepared (Jun. 19, 1997) | No Challenge | 15 seconds | >5.5 |
| Ex. II Prepared (Jun. 19, 1997) | 10% Milk | 15 seconds | >5.5 |
| UDDER GOLD PLUS Prepared (Jun. 19, 1997) | No Challenge | 15 seconds | 1.2 |
| UDDER GOLD PLUS Prepared (Jun. 19, 1997) | 10% Milk | 15 seconds | 0.1 |
| *Staphylococcus aureus* ATCC 6538 | | | |
| Ex. II Prepared (Jun. 19, 1997) | No Challenge | 15 seconds | >6.0 |
| Ex. II Prepared (Jun. 19, 1997) | 10% Milk | 15 seconds | 5.3 |
| UDDER GOLD PLUS Prepared (Jun. 19, 1997) | No Challenge | 15 seconds | 1.3 |
| UDDER GOLD PLUS Prepared (Jun. 19, 1997) | 10% Milk | 15 seconds | 0.6 |

After four weeks, Example II achieved a >5 log reduction after 15 seconds with and without a 10% milk challenge against both *Staphylococcus aureus* ATCC 6538 and *Escherichia coli* ATCC 11229. UDDER GOLD PLUS achieved a 1.2 log reduction against *Escherichia coli* ATCC 11229 in 15 seconds without milk, while achieving a 0.6 log reduction with the 10% milk challenge. Against *Staphylococcus aureus* ATCC 6538 UDDER GOLD PLUS achieved a log reduction of 1.3 without milk, and 0.6 with a 10% milk challenge.

Porcine Skin Test

An analysis was made to determine the antimicrobial activity of teat dips applied to porcine skin inoculated with *Staphylococcus aureus* ATCC 6538 and *Escherichia coli* ATCC 11229. Using the following Test Method:
1. One inch squares of sterile lyophilized porcine skin (Corethium™2, Johnson & Johnson UK) were rehydrated in sterile distilled water for 1 hour.
2. Hydrated skin squares were dipped into each teat dip formulation for 10 seconds and hung in a vertical position to allow excess to drain off.
3. The squares were then place din a sterile petri dish and inoculated with 10 microliters of a 24 hour broth culture for the organism to be tested. After inoculation, samples were allowed a contact time of 5 minutes.
4. Skin squares were then put in a tube containing 20 mL of the appropriate neutralizer.
5. Samples were then vortexed and dilutions of $10^{-1}$, $10^{-3}$, and $10^{-5}$ were plated in order to enumerate the survivors.
6. Plates were incubated at 37° C. for 48 hours.
7. A neutralization test was also performed.

Method Parameters:

| Test Substance | Active Ingredients |
|---|---|
| $ClO_2$ Example II Formulation Prepared Jun. 19, 1997) | 2.00% LAS $ClO_2$ |
| UDDER GOLD PLUS (Prepared Jun. 19, 1997) | $ClO_2$ |
| Water Control | None |

Test Systems:
*Staphylococcus aureus* ATCC 6538
*Escherichia coli* ATCC 11229
Test Temperature: Room Temperature
Exposure Time: 5 minutes
Subculture Medium: Tryptone Glucose Extract Agar
Incubation: 37° C. for 48 hours
Results:

TABLE 2

Zero Time

| Test Substance | Exposure Time to Teat Dip (min) | Log Reduction |
|---|---|---|
| *Staphylococcus aureus* ATCC 6538 | | |
| $ClO_2$ Example II Formula (Prepared Jun. 19, 1997) | 5 | 2.73 |
| UDDER GOLD PLUS (Prepared Jun. 19, 1997) | 5 | No Reduction |
| Water Control | 5 | N/A |
| *Escherichia coli* ATCC 11229 | | |
| $ClO_2$ Example II Formula (Prepared Jun. 19, 1997) | 5 | 1.78 |
| UDDER GOLD PLUS (Prepared Jun. 19, 1997) | 5 | 1.32 |
| Water Control | 5 | N/A |

Results:

One Week

| Test Substance | Exposure Time to Teat Dip (min) | Log Reduction |
|---|---|---|
| *Staphylococcus aureus* ATCC 6538 | | |
| UDDER GOLD PLUS (Prepared Jun. 19, 1997) | 5 | No Reduction |
| $ClO_2$ Example II Formula (Prepared Jun. 19, 1997) | 5 | 3.48 |
| Water Control | 5 | N/A |
| *Escherichia coli* ATCC 11229 | | |
| UDDER GOLD PLUS (Prepared Jun. 19, 1997) | 5 | 0.20 |
| $ClO_2$ Example II Formula (Prepared Jun. 19, 1997) | 5 | 1.83 |
| Water Control | 5 | N/A |

Results:

Two Weeks

| Test Substance | Exposure Time to Teat Dip (min) | Log Reduction |
|---|---|---|
| *Staphylococcus aureus* ATCC 6538 | | |
| UDDER GOLD PLUS (Prepared Jun. 19, 1997) | 5 | No Reduction |
| $ClO_2$ Example II Formula (Prepared Jun. 19, 1997) | 5 | 3.52 |
| Water Control | 5 | N/A |
| *Escherichia coli* ATCC 11229 | | |
| UDDER GOLD PLUS (Prepared Jun. 19, 1997) | 5 | 0.08 |
| $ClO_2$ Example II Formula (Prepared Jun. 19, 1997) | 5 | 0.60 |
| Water Control | 5 | N/A |

Results:

Three Weeks

| Test Substance | Exposure Time to Teat Dip (min) | Log Reduction |
|---|---|---|
| *Staphylococcus aureus* ATCC 6538 | | |
| UDDER GOLD PLUS (Prepared Jun. 19, 1997) | 5 | No Reduction |
| $ClO_2$ Example II Formula (Prepared Jun. 19, 1997) | 5 | 2.26 |
| Water Control | 5 | N/A |
| *Escherichia coli* ATCC 11229 | | |
| UDDER GOLD PLUS (Prepared Jun. 19, 1997) | 5 | 0.77 |
| $ClO_2$ Example II Formula (Prepared Jun. 19, 1997) | 5 | 1.73 |
| Water Control | 5 | N/A |

Results:

Four Weeks

| Test Substance | Exposure Time to Teat Dip (min) | Log Reduction |
|---|---|---|
| *Staphylococcus aureus* ATCC 6538 | | |
| UDDER GOLD PLUS (Prepared Jun. 19, 1997) | 5 | 0.19 |
| $ClO_2$ Example II Formula (Prepared Jun. 19, 1997) | 5 | 2.78 |
| Water Control | 5 | N/A |
| *Escherichia coli* ATCC 11229 | | |
| UDDER GOLD PLUS (Prepared Jun. 19, 1997) | 5 | 0.07 |
| $ClO_2$ Example II Formula (Prepared Jun. 19, 1997) | 5 | 1.72 |
| Water Control | 5 | N/A |

These test results show the compositions of the invention are superior in these anti-microbial tests to a quality commercial teat dip. These data are representative in anti-microbial properties of the exemplary formulations of the invention.

The teat dip compositions of the invention using nonanoic acid and a sulfonate material in a formulation with 1-propanol, were tested for their properties in coating and forming a useful antimicrobial layer that maintains a sufficient quantity of material on the animal. A simulated test was conducted involving a test tube. In the method a Kimax® brand glass test tube (20 mm×150 mm) is weighted, and dipped approximately 2 inches into the teat dip being tested. The test tube is then removed from the dip and placed on hanging rack for 10 minutes above a beaker that was previously weighted. At the end of 10 minutes the beaker and the test tube are each weighed again and the data is entered into the table. The dry weight is obtained by allowing the resulting teat dip film to dry for 24 hrs.

Simulated Teat Dipping Test
UDDER GOLD PLUS

| Sample Name | Wet Wt. UDDER GOLD PLUS 1 | Wet Wt. UDDER GOLD PLUS 2 | Dry Wt. UDDER GOLD PLUS 1 | Dry Wt. UDDER GOLD PLUS 2 |
|---|---|---|---|---|
| Beaker Tare | 110.3762 | 106.9215 | 110.3762 | 106.9215 |
| Test Tube Tare | 24.5295 | 18.9019 | 24.5295 | 18.9019 |
| Beaker @ 10 min. | 111.7136 | 108.1773 | 110.5015 | 107.0377 |
| Test Tube @ 10 min. | 24.6747 | 19.0028 | 24.5459 | 18.9151 |
| Product on Test Tube | 0.1452 | 0.1009 | 0.0164 | 0.0132 |
| Product in Beaker | 1.3374 | 1.2558 | 0.1253 | 0.1162 |
| % Product Retained | 9.79% | 7.44% | 11.57% | 10.20% |
| % Product Lost | 90.21% | 92.56% | 88.43% | 89.80% |

Simulated Teat Dipping Test
Composition of Example I

| Sample Name | Wet Wt. Example I | Wet Wt. Example I | Dry Wt. Example I | Dry Wt. Example I |
|---|---|---|---|---|
| Beaker Tare | 108.0534 | 107.0201 | 108.0534 | 107.0201 |
| Test Tube Tare | 25.0294 | 24.9161 | 25.0294 | 24.9161 |
| Beaker @ 10 min. | 108.3413 | 107.3925 | 108.1192 | 107.1081 |
| Test Tube @ 10 min. | 25.1733 | 25.0665 | 25.0596 | 24.9432 |
| Product on Test Tube | 0.1439 | 0.1504 | 0.0302 | 0.0271 |
| Product in Beaker | 0.2879 | 0.3724 | 0.0658 | 0.0880 |
| % Product Retained | 33.33% | 28.77% | 31.46% | 23.54% |
| % Product Lost | 66.67% | 71.23% | 68.54% | 76.46% |

Comments: Wet Wt. = 10 minutes  Formula Example I = 2.5% 1-Propanol
Dry Wt. = 24 hours  1.5% C9  17.0% NAS A brief examination of the tabulated data show that the rheology of the material of Example I maintains a larger quantity of material on the simulated animal when compared to the rheology of the commercial teat dip formulation. These data suggest that the composition of Example I would be somewhat more effective in mastitis treatment because the formulations of the invention would maintain a larger quantity of treating composition in a longer lasting film than the commercial materials. In other testing we have found that the identity of the antibacterial material, carboxylic acid, fatty acid, phosphoric acid or sulfonic acid, does not significantly change the rheology of the material and a fully formulated material having rapid initial kill and long term kill can be formulated in a long lasting film-forming composition.

The following Examples show a preferred emollient/humectant formulation technology.

EXAMPLE XV

Chlorine Dioxide Teat Dip
Acidulant

| Item | Ingredients | Wt % |
|---|---|---|
| 1 | Deionized Water | 71.92 |
| 2 | KOH, 45% | 1.10 |
| 3 | Benzoic Acid | 0.20 |
| 4 | Kelzan T | 0.30[1] |
| 5 | Laneto 50 | 1.00 |
| 6 | Sorbitol, 70% (Glucitol) | 6.43 |
| 7 | LAS, 97% | 2.00[2] |
| 8 | Lactic Acid, 88% | 2.95 |
| 9 | Elvanol Premix, 10% | 10.00 |
| 10 | Pylaklor Yellow LLX1-10192, 5.0% | 4.00 |
| 11 | Sunsperse Blue GS | 0.10[3] |
| TOTAL | | 100.00 |

[1] stir at least 1 hr./check clarity
[2] stir 10 minutes
[3] pH = → should be ~2.70

Mixing Instructions:

1. Add item 1 to mix tank. Turn on agitator. Slowly add item 2.
2. Add item 3 and mix until dissolved.
3. Charge item 4 with water through an eductor funnel, Hercules mixing tee or manually continue agitation at a slow addition rate. Lumping may result if added too quickly. Mix for 1 hour or until item 4 is completely solubilized.

Have QC check for clarity

Note: Complete solubilization is crucial before additional items are added.

4. Add items 5 and 6. Mixing well between each addition.
5. Slowly add item 7 to avoid high concentrations of localized acidity. Mix—10 minutes.
6. Slowly add item 8 and mix well. Add item 9 and mix well.
7. Add items 10 and 11. Final mix is 30 mintues.
8. Transfer and filter batch with 80 (3/16 inch) mesh strainer. Sample for QC.

Activator
Sodium Chlorite Solution - 6.25% Aqueous

| Item | Ingredients | Wt % |
|---|---|---|
| 1 | Deionized Water | 75.00 |
| 2 | Sodium Chlorite, 25% | 25.00 |
| TOTAL | | 100.00 |

Mixing Instructions:

1. Add item 1 to the mix tank.
2. Slowly add item 2 (mix ratio 3376 gs. Acidualnt with 93 gs. Of the Activator) and mix well.

EXAMPLE XVI

Chlorine Dioxide Teat Dip; Pre DipFormula

Purpose: Prepare a 1000 g batch of the following experimental predip formula for physical stability testing.

| Predip Formula | | |
|---|---|---|
| Item | Ingredients | Wt % |
| 1 | Deionized Water | 91.580 |
| 2 | KOH, 45% | 1.230 |
| 3 | Benzoic Acid | 0.200 |
| 4 | Kelzan T | 0.100[1] |
| 5 | Neodol 25-9 | 0.500 |
| 6 | Sorbitol, 70% (Glucitol) | 1.430 |
| 7 | LAS, 97% | 2.000[2] |
| 8 | Lactic Acid, 88% | 2.950 |
| 9 | Sunsperse Blue GS | 0.010[3] |
| TOTAL | | 100.00 |

[1]stir at least 1 hr./check clarity
[2]stir 10 minutes
[3]pH = ~2.70

Mixing Instructions:
1. Add item to mix tank. Turn on agitator. Add item 2 and mix until dissolved.
2. Slowly add item 3.
3. Charge item 4 with water through an eductor funnel, Hercules mixing tee or manually continue agitation at a slow addition rate. Lumping may result if added too quickly. Mix for 1 hour or until item 4 is completely solubilized. Have QC check for clarity
4. Add items 5 and 6. Mixing well between each addition.
5. Slowly add item 7 to avoid high concentrations of localized acidity. Mix 10 minutes.
6. Slowly add item 8 and mix well.
7. Add item 9. Final mix is 30 minutes.
8. Transfer and filter batch with 80 (3/16 inch) mesh strainer. Sample for QC.

| Activator-Sodium Chlorite Solution - 6.25% | | |
|---|---|---|
| Item | Ingredients | Wt % |
| 1 | Deionized Water | 75.00 |
| 2 | Sodium Chlorite, 25% | 25.00 |
| TOTAL | | 100.00 |

Mixing Instructions:
1. Add item 1 to the mix tank.
2. Slowly add item 2 (mix ratio 3376 gs. Predip Formula with 93 gs. Of the Activator) and mix well.

EXAMPLE XVII

Chlorine Dioxide Teat Dip; Pre/Post Dip Formula
Purpose: Prepare a 5 gallon batch of the following experimental pre/post dip

| Pre/Post Formula | | |
|---|---|---|
| Item | Ingredients | Wt % |
| 1 | Deionized Water | 83.46 |
| 2 | KOH, 45% | 1.25 |
| 3 | Benzoic Acid | 0.20 |
| 4 | Kelzan T | 0.10[1] |
| 5 | Neodol 25-9 | 0.50 |
| 6 | Laneto 50 | 1.00 |

-continued

| Pre/Post Formula | | |
|---|---|---|
| Item | Ingredients | Wt % |
| 7 | Sorbitol, 70% (Glucitol) | 6.43 |
| 8 | LAS, 97% | 2.06[2] |
| 9 | Lactic Acid, 88% | 2.95 |
| 10 | Pylaklor Yellow LX-10192, 5.0% | 2.00 |
| 11 | Sunsperse Blue GS | 0.05[3] |
| TOTAL | | 100.00 |

[1]stir at least 1 hr./check clarity
[2]stir 10 minutes
[3]pH = ~2.70

Mixing Instructions:
1. Add item 1 to mix tank. Turn on agitator. Slowly add item 2.
2. Add item 3 and mix until dissolved.
3. Charge item 4 with water through an eductor funnel, Hercules mixing tee or manually continue agitation at a slow addition rate. Lumping may result if added too quickly. Mix for 1 hour or until item 4 is completely solubilized. Have QC check for clarity
4. Add items 5, 6 and 7. Mixing well between each addition.
5. Slowly add item 8 to avoid high concentrations of localized acidity. Mix until dispersed—approximately 10 minutes.
6. Slowly add item 9 and mix well.
7. Add items 10 and 11. Final mix is 30 minutes.
8. Transfer and filter batch with 80 (3/16 inch) mesh strainer. Sample for QC.

| Activator Formula-Sodium Chlorite Solution - 6.25% | | |
|---|---|---|
| Item | Ingredients | Wt % |
| 1 | Deionized Water | 75.00 |
| 2 | Sodium Chlorite, 25% | 25.00 |
| TOTAL | | 100.00 |

Mixing Instructions:
1. Add item 1 to the mix tank.
2. Slowly add item 2 and mix well.

EXAMPLE XVIII

Conc. Chlorine Dioxide Teat Dip; Udder Wash & Teat Dip Formula
Purpose: Prepare a 100 g batch of the following experimental udder wash & teat dip formula for stability testing at 122° F. temperature condition.

| CONC Formula | | |
|---|---|---|
| Item | Ingredients | Wt % |
| 1 | Deionized Water | 27.60 |
| 2 | KOH, 45% | 0.05 |
| 3 | Benzoic Acid | 0.20 |
| 4 | Sunsperse Blue GS | 1.10 |
| 5 | Propylene Glycol | 11.90 |
| 6 | Neodol 25-9 | 2.15 |

| | -continued | |
|---|---|---|
| 7 | LAS, 97% | 2.15 |
| 8 | Laneto 50 | 5.50 |
| 9 | Sortitol, 70% | 30.35 |
| 10 | Lactic Acid, 88% | 19.00 |
| | TOTAL | 100.00[1] |

| Activator Formula: 3.125% Sodium Chlorite | | |
|---|---|---|
| Item | Ingredients | Wt % |
| 1 | Deionized Water | 87.50 |
| 2 | Sodium Chlorite, 25% aqueous | 12.50 |
| | TOTAL | 100.00 |

Mix Ratios:

| Acidulant Base (g) | Activator | Water |
|---|---|---|
| 1 | 1 part | 20 parts |

Physical Stability:

| 122° F. | After 24 hrs. at 122° F., the above product IS stable. After 4 days at 122° F., the above product IS stable. After 1 week at 122° F., the above product IS stable |
|---|---|

Comments:

| Control | Continue (1 + 1 + 20) Ph = 2.41 |
|---|---|
| Control | Continue Activator Conc pH = 1.6 |
| Formula K | use-dil (1 + 1 + 20) pH = 2.62 |
| $ClO_2$ | 885 ppm |

[1]product looked good - no particulates

EXAMPLE XIX

| Conc. Chlorine Dioxide Teat Dip Acid Formula | | |
|---|---|---|
| Item | Ingredients | Wt % |
| 1 | Deionized Water | 27.60 |
| 2 | KOH, 45% | 0.05 |
| 3 | Benzoic Acid | 0.20 |
| 4 | Sunsperse Blue GS Dye | 1.10 |
| 5 | Propylene Glycol | 11.90 |
| 6 | Neodol 25-9 nonionic | 2.15 |
| 7 | LAS, 97% anionic sulf. | 2.15 |
| 8 | Laneto 50 (EO)$_{75}$ - lanolin | 5.50 |
| 9 | Sortitol, 70% | 30.35 |
| 10 | Lactic Acid, 88% | 19.00 |
| | TOTAL | 100.00 |

| Activator Formula: 3.125% Sodium Chlorite | | |
|---|---|---|
| Item | Ingredients | Wt % |
| 1 | Deionized Water | 87.50 |
| 2 | Sodium Chlorite, 25% | 12.50 |
| | TOTAL | 100.00 |

Mix Ratios:
1 part Acid Formula: 1 part Activator Formula
Comments:
$ClO_2$ titr. RTU=885 ppm The following Examples and data demonstrate that the dyed system can be made resistant, due to the addition of urea, to dye bleaching from the chlorine dioxide generated in the final dip. The product shown is the acid part or base dip. To this acid part is added a sodium chlorite part. The acid adjusts pH and reacts with sodium chlorite ($NaClO_2$) to form chlorine dioxide.

EXAMPLE XX

| Barrier Teat Dip Base Part (Part 1) | |
|---|---|
| RAW MATERIAL | WT-% |
| DI water | 70.46 |
| Polyvinyl alcohol | 1.00 |
| DI water | 10.00 |
| KOH (45% aqueous) | 0.40 |
| Sodium benzoate | 0.18 |
| Xanthan gum | 0.30 |
| Lactic acid | 2.95 |
| Urea, prilled | 1.50 |
| Lanolin ethoxylate | 1.00 |
| Propylene glycol | 10.00 |
| Linear Dodecyl benzene sulfonic acid | 2.06 |
| FD&C Blue Dye #1 | 0.05 |
| FD&C Yellow Dye #5 | 0.10 |
| TOTAL | 100.00 |

| Activator Part ($ClO_2^{-1}$ Formula; pH = 12.3) (Part 2) | | |
|---|---|---|
| Ingredients | Wt % | Grams |
| Deionized Water | 85.00 | 850.00 |
| Sodium Chlorite, 25% | 15.00 | 150.00 |
| TOTAL | 100.00 | 1000.00 |

The following test examples were prepared similarly to Example XX to test the capacity of the systems of the invention to stabilize the color of FD&C yellow dye #5 and FD&C blue dye #1 in the oxidative enviroment of the formulated materials with a range of chlorite, colorant and urea concentrations.
These data are displayed in FIG. 4.

TEST EXAMPLE XXI-A-B-C, EXAMPLE XXII-A-B-C and EXAMPLE XXIII-A-B-C

| Sample | $ClO_2^{-1}$ (ppm) | FDC Y #5 (%) | FDC B #1 (%) | Urea (%) | Urea g of 100% | Base Dip Conc (mL) | Make up Water (%) | Total Vol. (mL) |
|---|---|---|---|---|---|---|---|---|
| XXIA | 479 | 0.10 | 0.05 | 0.50 | 0.50 | 90.00 | 6.58 | 93.42 |
| XXIB | 479 | 0.10 | 0.05 | 1.00 | 1.00 | 90.00 | 5.58 | 94.42 |
| XXIC | 479 | 0.10 | 0.05 | 1.50 | 1.50 | 90.00 | 4.58 | 95.42 |
| XXIIA | 638 | 0.10 | 0.05 | 0.50 | 0.50 | 90.00 | 6.33 | 93.67 |
| XXIIB | 638 | 0.10 | 0.05 | 1.00 | 1.00 | 90.00 | 5.33 | 94.67 |
| XXIIC | 638 | 0.10 | 0.05 | 1.50 | 1.50 | 90.00 | 4.33 | 95.67 |
| XXIIIA | 825 | 0.10 | 0.05 | 0.50 | 0.50 | 90.00 | 6.03 | 93.97 |
| XXIIIB | 825 | 0.10 | 0.05 | 1.00 | 1.00 | 90.00 | 5.03 | 94.97 |
| XXIIIC | 825 | 0.10 | 0.05 | 1.50 | 1.50 | 90.00 | 4.03 | 95.97 |

Increasing concentrations of urea clearly stabilized the color in the formulations.

EXAMPLE XXIII

| RAW MATERIAL | CONTROL 1 | 3 |
|---|---|---|
| DI water | 32.6 | 35.6 |
| Benzoic acid | 0.2 | 0.2 |
| KOH 45% | 0.4 | 0.4 |
| Propylene glycol | 42 | 38 |
| Neodol 25-9 | 2.15 | 1.15 |
| Lactic acid 88% | 12.5 | 12.5 |
| Lanolin | 5.5 | 5.5 |
| Urea | 0 | 1 |
| Pluronic F 68 | 0 | 1 |
| LAS acid | 2.15 | 2.15 |
| FD&C Yellow 5 CAS # 12225-21-7 | 2.5 | 2.5 |
| 100% pH | 1.76 | 1.85 |

This example shows a formulation made with and without urea stabilizing the organic dye. These materials were equally effective sanitizer materials against a microbial challenge.

The following Examples were made to show that the urea color stability system also lengthens the useful lifetime of the blended materials. The urea slows chlorine dioxide release is delayed resulting in the generation of chlorine dioxide at a somewhat lower but effective concentration for a greater amount of effective life.

EXAMPLE XXIV

| RAW MATERIAL | A (%) | B (%) | C (%) |
|---|---|---|---|
| DI water | 45.600 | 45.800 | 44.038 |
| KOH 45% | 0.400 | 0.400 | 0.385 |
| Benzoic acid | 0.200 | 0.200 | 0.192 |
| Propylene glycol | 30.000 | 30.000 | 28.846 |
| Neodol 25-9 | 2.150 | 2.150 | 2.067 |
| Lanolin | 5.500 | 5.500 | 5.288 |
| Lactic acid | 10.500 | 11.000 | 14.423 |
| LAS acid | 2.150 | 2.200 | 2.115 |
| Urea | 2.000 | 1.250 | 1.202 |
| FD&C Blue 1 | 1.500 | 1.500 | 1.4442 |
| TOTAL | 100.000 | 100.000 | 100.000 |

Chlorine Dioxide Profile of Examples XXIV A–C

| Hours | XXIV A ppm $ClO_2$ | XXIV B ppm $ClO_2$ | XXIV C ppm $ClO_2$ |
|---|---|---|---|
| 0.50 | 6.4 | 8.90 | 12.0 |
| 0.30 | — | 11.6 | 14.4 |
| 0.50 | 9.4 | 13.0 | 16.6 |
| 1.00 | 16.3 | 16.9 | 21.8 |
| 1.50 | 17.0 | 16.0 | 20.0 |
| 3.00 | 19.6 | 24.9 | 32.9 |
| 4.00 | 24.9 | 34.0 | 38.7 |
| 6.00 | 30.1 | 44.5 | 56.7 |
| 24.00 | 67.0 | 93.0 | 121.0 |

These data show an important aspect of the invention. The use of urea in a chlorine dioxide generating system appears to slow the release of chlorine dioxide after the acidulant part is combined with the chlorite part. The data in the table shows that the increasing concentration of the urea reduces the concentration of available chlorine dioxide and as a result delays the generation of chlorine dioxide, extending the effective lifetime of the treatment material. This demonstrates that the urea component asked to both stabilize color and to extend the effective lifetime (chlorite concentration) of the treatment material.

EXAMPLE XXV

Materials prepared for long term stability testing

| RAW MATERIAL | A | B | C | D |
|---|---|---|---|---|
| DI water | 41.800 | 39.250 | 36.600 | 33.850 |
| KOH 45% | 0.400 | 0.400 | 0.400 | 0.400 |
| Benzoic acid | 0.200 | 0.200 | 0.200 | 0.200 |
| Propylene glycol | 30.000 | 30.000 | 30.000 | 30.000 |
| Neodol 25-9 | 2.150 | 2.150 | 2.150 | 2.150 |
| Lanolin | 5.500 | 5.500 | 5.500 | 5.500 |
| Lactic acid | 15.000 | 15.000 | 15.000 | 15.000 |
| LAS acid | 2.200 | 4.000 | 6.000 | 8.000 |
| KOH 45% | 0.000 | 0.750 | 1.400 | 2.150 |
| Urea | 1.250 | 1.250 | 1.250 | 1.250 |
| FD&C Blue 1 | 1.500 | 1.500 | 1.500 | 1.500 |
| TOTAL | 100.000 | 100.000 | 100.000 | 100.000 |
| 100% pH | 1.79 | 1.70 | 1.69 | 1.70 |
| Appearance of Products w/o Dye | Initially Hazy | Initially Hazy | Initially Hazy | Clear |

These materials were storage stable at common storage temperatures and provided were effective sanitizer materials over an extended period. Initial haze cleared after less than one week. The materials were freeze-proof.

EXAMPLE XVI

Chemiluminescent Teat Dips

In the invention, the chemiluminescence process involves three components, an oxidizer (usually hydrogen peroxide or an indirect source of hydrogen peroxide), oxalate ester or amide (examples are Figures (I) and (II)). These esters or amides can be water insoluble and utilize oil-in-water emulsions or they can be water soluble. Likewise, oil soluble fluorescers and/or water soluble fluorescers may be used. The oil phase of the emulsified version may prove useful for solubilizing the fluorescer as well as the oxalate ester or amide.

Additionally, the chemiluminescent system may use Luminol type chemistry, and these may include an oxidizer (again, usually hydrogen peroxide or an indirect source of hydrogen peroxide), Luminol, a metal ion, (i.e., Cu (II) added as $Cu(SO_4)_2$) and a carbonate buffer system at pH 8–10 is typical.

Suitable oxalate esters include: 4,4'-{oxalyl bis (3-nitrobenzene sulfonic acid)} and oxalyl bis (N-oxysuccinimide) and others.

Composition of Two Part System

EXAMPLE (I)

Activator Formula (Part I)

| INGREDIENT | % | Wt (grams) |
|---|---|---|
| 4,4'-(oxalyl bis (3-nitrobenzene sulfonic acid)) | 50.0 | 0.5 |
| Rhodamine B (C.I. 45170) | 50.0 | 0.5 |

Base Formula (Part II)

| INGREDIENT | % | Wt (grams) |
|---|---|---|
| Water | 88.0 | 880.0 |
| Hydrogen peroxide (35% w/v) | 3.0 | 30.0 |
| Lactic acid | 2.8 | 28.0 |
| Glycerine | 6.0 | 60.0 |
| Xanthan gum | 0.2 | 2.0 |

EXAMPLE (II)

Activator Formula (Part I)

| INGREDIENT | % | Wt (grams) |
|---|---|---|
| Oxalyl bis (N-oxysuccinimide) | 50.0 | 0.5 |
| Rhodamine B (C.I. 45170) | 50.0 | 0.5 |

Base Formula (Part II)

| INGREDIENT | % | Wt (grams) |
|---|---|---|
| Water | 88.0 | 880.0 |
| Hydrogen peroxide (35% w/v) | 3.0 | 30.0 |
| Lactic acid | 2.8 | 28.0 |
| Glycerine | 6.0 | 60.0 |
| Xanthan gum | 0.2 | 2.0 |

Suitable oxalate amides include:

EXAMPLE (III)

Activator Formula (Part I)

| INGREDIENT | % | Wt (grams) |
|---|---|---|
| Bis[2,6-dichloro-4-[(2-dimethylaminoethyl)methylsulfamoyl]phenyl}oxalate dihydrochloride | 50.0 | 0.5 |
| Rhodamine B (C.I. 45170) | 50.0 | 0.5 |

Base Formula (Part II)

| INGREDIENT | % | Wt (grams) |
|---|---|---|
| Water | 88.0 | 880.0 |
| Hydrogen peroxide (35% w/v) | 3.0 | 30.0 |
| Lactic acid | 2.8 | 28.0 |
| Glycerine | 6.0 | 60.0 |
| Xanthan gum | 0.2 | 2.0 |

EXAMPLE (IV)

Activator Formula (Part I)

| INGREDIENT | % | Wt (grams) |
|---|---|---|
| CCPO (bis2,4,5-trichlorophenyl-6-carbopentoxyphenyl)oxalate | 50.0 | 0.5 |
| 1-Chloro-9,10-bis(phenynyl)anthracene | 50.0 | 0.5 |

Base Formula (Part II)

| INGREDIENT | % | Wt (grams) |
|---|---|---|
| Water | 87.05 | 870.5 |
| Hydrogen peroxide (35% w/v) | 3.0 | 30.0 |
| Lactic acid | 2.8 | 28.0 |
| Glycerine | 6.0 | 60.0 |
| Xanthan gum | 0.4 | 4.0 |
| Glyceryl laurate (Monolaurin) | 0.5 | 5.0 |
| Nonylphenol ethoxylate (9.5 EO) | 0.25 | 2.5 |

An example of an indirect source of hydrogen peroxide is sodium perborate. The following is an example of a teat dip formula which substitutes sodium perborate for hydrogen peroxide.

EXAMPLE (V)

Activator Formula (Part I)

| INGREDIENT | % | Wt (grams) |
|---|---|---|
| Bis[2,6-dichloro-4-[(2-dimethylaminothyl)methylsulfamoyl]phenyl}oxalate dihydrochloride | 50.0 | 0.5 |
| Rhodamine B (C.I. 45170) | 50.0 | 0.5 |

Base Formula (Part II)

| INGREDIENT | % | Wt (grams) |
|---|---|---|
| Water | 88.0 | 880.0 |
| Sodium perborate | 3.0 | 30.0 |
| Lactic acid | 2.8 | 28.0 |
| Glycerine | 6.0 | 60.0 |
| Xanthan gum | 0.2 | 2.0 |

EXAMPLE (VI)

Activator Formula (Part I)

| INGREDIENT | % | Wt (grams) |
|---|---|---|
| Sodium chlorite | 9.09 | 1.0 |
| Sodium perborate | 90.91 | 10.0 |

Base Formula (Part II)

| INGREDIENT | % | Wt (grams) |
|---|---|---|
| Water | 90.95 | 909.5 |
| Lactic acid | 2.75 | 27.5 |
| Glycerine | 6.0 | 60.0 |
| Xanthan gum | 0.20 | 2.0 |
| Rhodamine B (C.I. 45170) | 0.05 | 0.5 |

| -continued | | |
|---|---|---|
| Bis{2,6-dichloro-4-[(2-dimethylaminoethyl) methylsulfamoyl]phenyl}oxalate dihydrochloride | 0.05 | 0.5 |

To initiate the chemiluminiscence phenomena, the entire contents of the activator (Part I) is mixed thoroughly, with the entire contents of the respective base (Part II) at ambient temperatures.

DETAILED DISCUSSION OF THE DRAWINGS

Figure 1B:
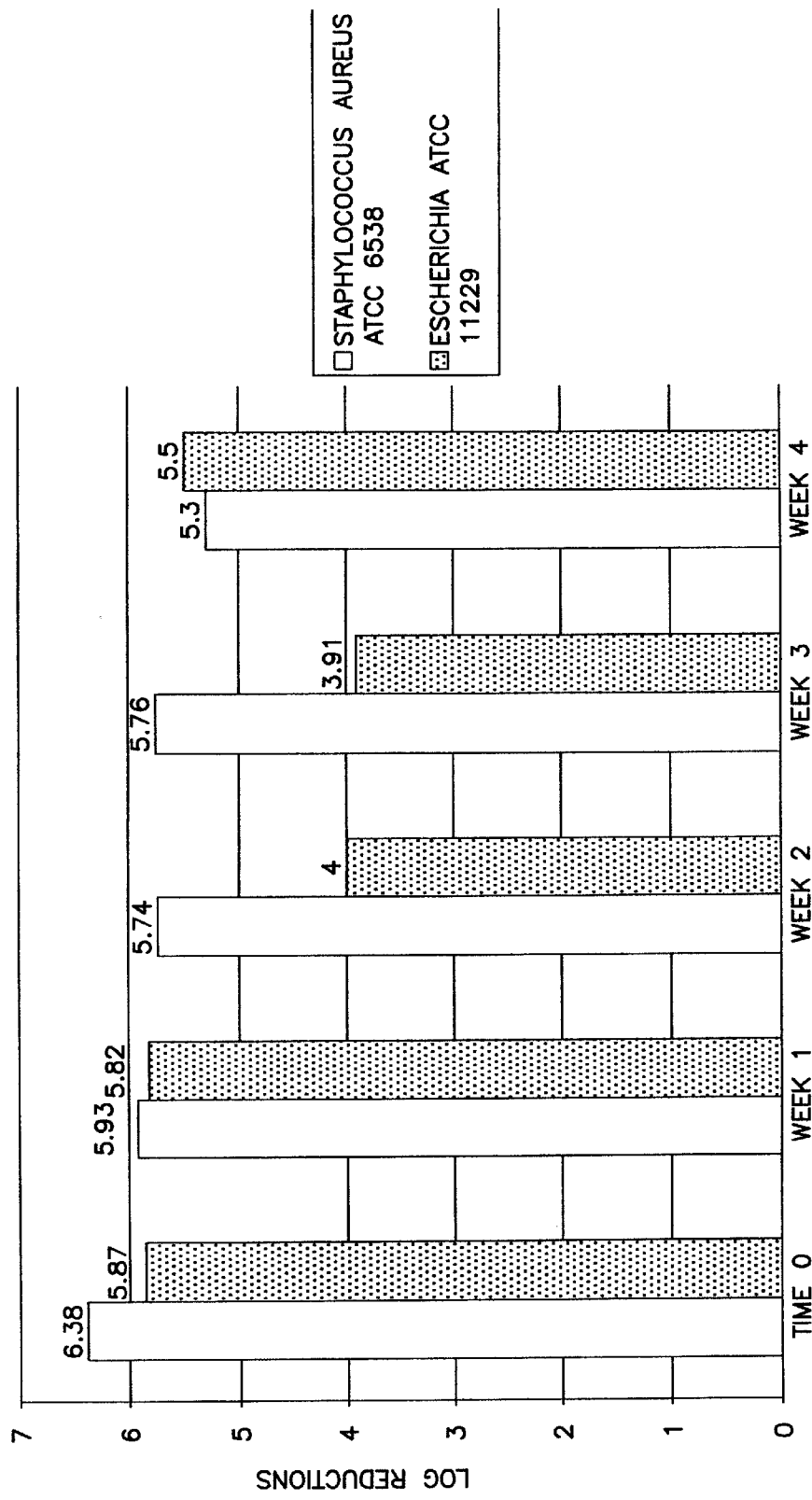

FIG. 1A and FIG. 1B are a graphical representations of the data shown in the tables from page 46 to 50 showing the results of a four week biocidal efficacy analysis of Example II using the food contact sanitizing protocol shown at pages 41 to 45 preceding the data in the specification. Clearly, from zero time through four weeks the composition of Example II had a kill substantially greater than a 5 log reduction in microbial populations of both model microorganisms. This data was taken without a milk challenge. However, FIG. 1B shows, within experimental error, similar properties using the same food contact sanitizing protocol with a 10% milk soil challenge. The week 2 and week 3 kill of E. coli is not easily explained in view of the 5.5 log reduction obtained in week 4 for that model microorganism. However, overall the results are strikingly successful in reducing microorganism populations on food contact surfaces.

Figure 1C:
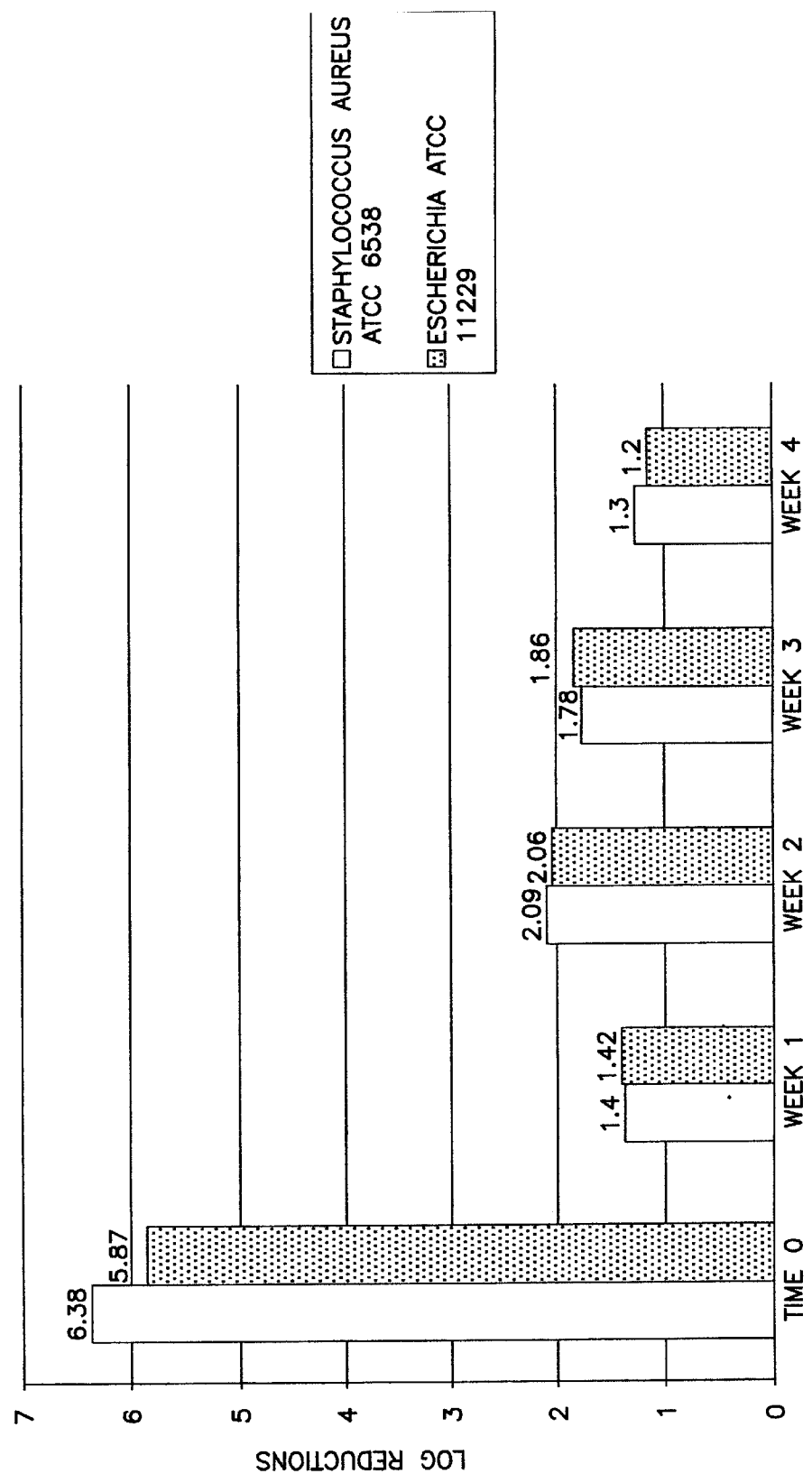
Figure 1D:
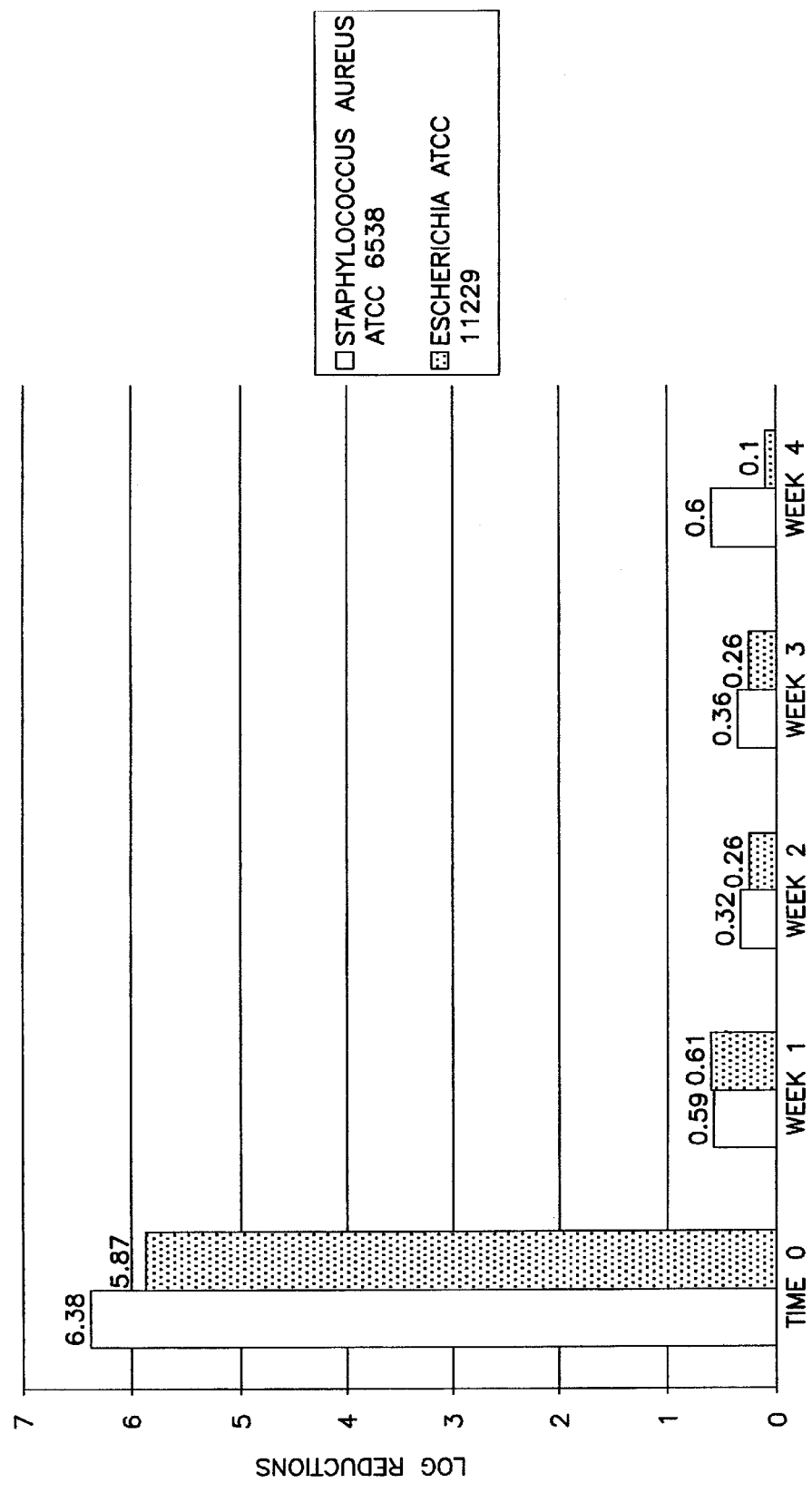

FIG. 1C and FIG. 1D are graphical representations of data showing the results of the four week biocidal efficacy analysis of a commercial teat dip composition sold under the tradename UDDER GOLD PLUS.

The superiority in performance of the composition of Example II when compared to the UDDER GOLD PLUS compositions is marked particularly in weeks 1 through 4.

Figure 2A:
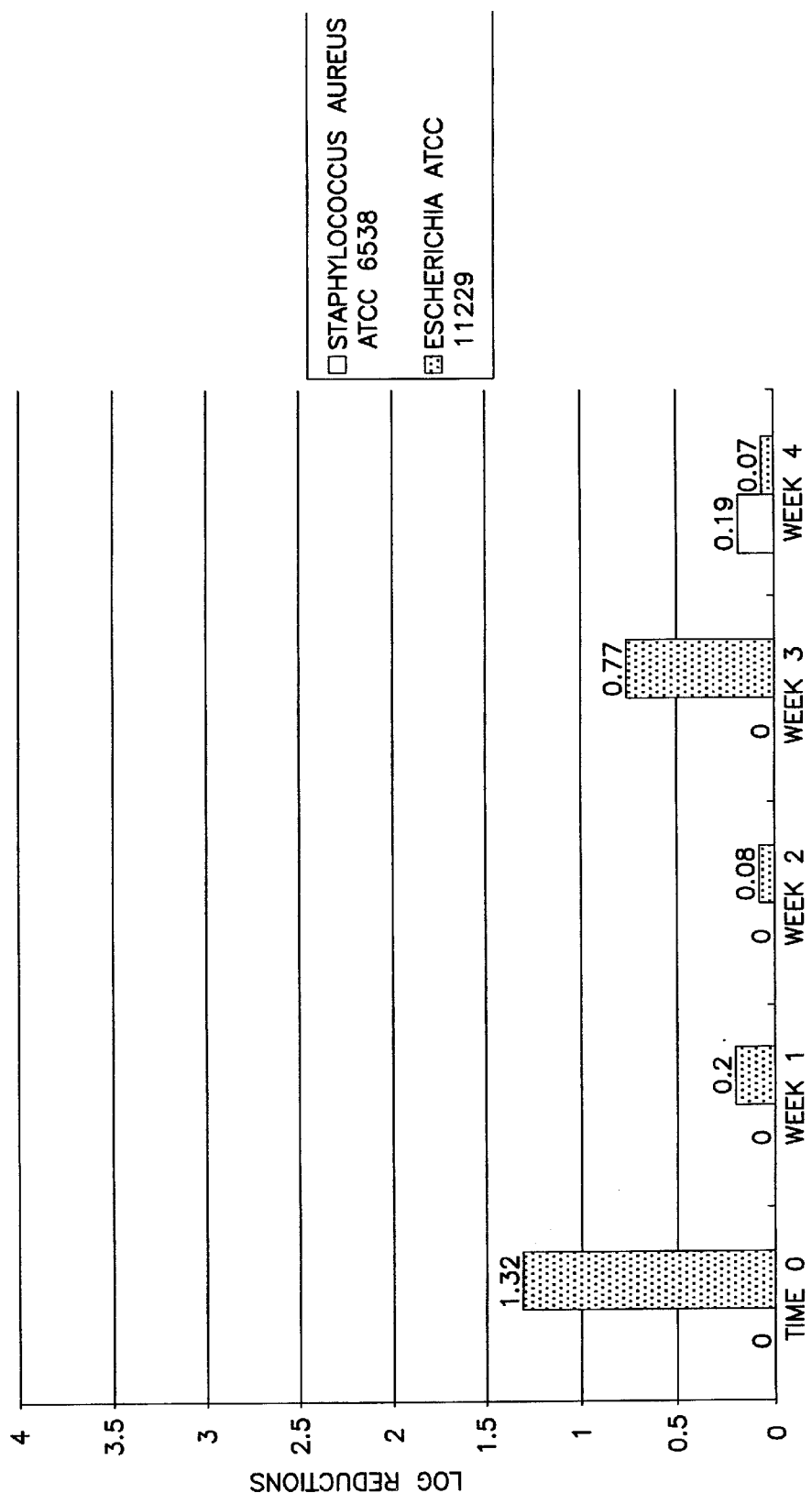
FIG. 2A is a graph showing the four week efficacy analysis of the UDDER GOLD PLUS formulation using the porcein skin test protocol.

FIG. 2A, a graphical representation of the data shown in the tables from page 52 to 56 is a four week efficacy analysis of the UDDER GOLD PLUS chlorine dioxide teat dip formulation measured using the procein skin protocol at pages 51 to 52 in the specification. In all test periods the material failed to achieve greater than a 2 log reduction.

FIG. 2B, prepared from the corresponding data given in the forementioned tables, shows a four week efficacy analysis of Example II using the porcein skin protocol. Clearly, under these more difficult conditions using the porcein skin substrate as a test vehicle, the log reductions in kill are not as great as those for food contact surfaces, however, the biocidal efficacy of Example II exceeded that of the well regarded UDDER GOLD PLUS chlorine dioxide formulations.

Figure 3:
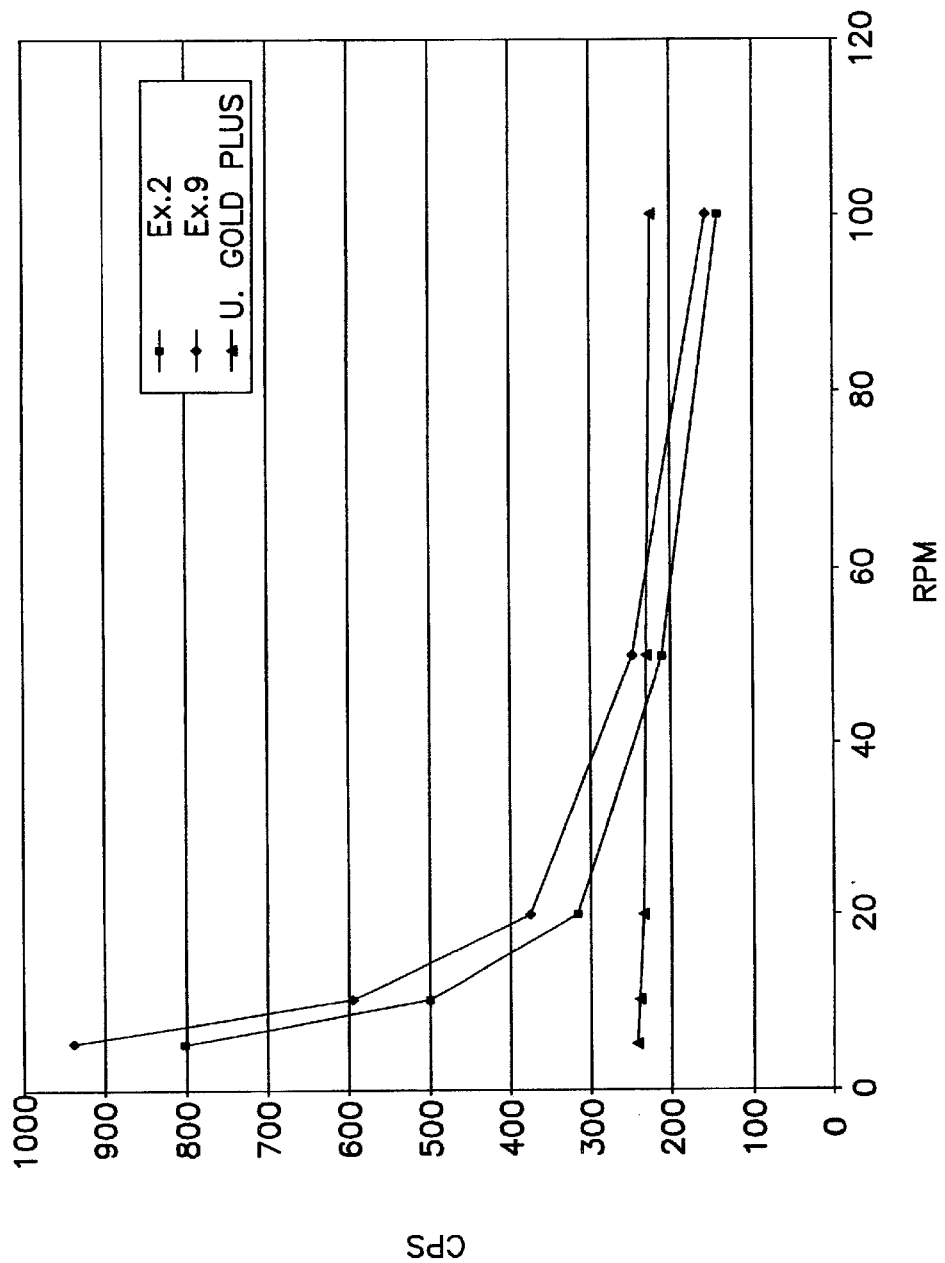
FIG. 3 is a graph showing the change in viscosity with changing shear of two exemplary teat dips, Examples II and IX, of the application compared to the UDDER GOLD PLUS formulation.

FIG. 3, shows a graph of the change in viscosity measured in centipoise plotted against shera rpm for UDDER GOLD PLUS and Example II and Example IX of the invention. The examples of the invention should show classic non-neutonian or nonlinear viscosity with respect to shear. At low shear, i.e., low rpm, the viscosity is high. As shear increases, viscosity drops. In sharp contrast, viscosity of the UDDER GOLD PLUS formulation shows much less pseudoplastic behavior. The viscosity is substantially constant as shear or rpm increases. This viscosity information is consistent with the data of the previous table and demonstrates that the viscoelastic behavior of the compositions of the invention are likely to coat and adhere to teat tissue more efficiently than UDDER GOLD PLUS. Since the materials are sheared somewhat upon application, the materials will flow on to the teat surface. However, when shear is removed, the teat dips obtain high viscosity and tend to adhere more tenaciously than a composition such as UDDER GOLD PLUS having linear viscosity. The substantial difference in viscosity at low shear (low rpm) demonstrates that the materials should coat the teat with substantially more material and after drying have a more effective environmental barrier.

The procedure is as follows. Place ~500 mls of the experimental teat dip in 600 ml beaker. Record viscosity measurements at various rpms. Apparatus: Brookfield RVT Viscometer, spindle #1 and 2, various rpm (see chart below). Start Temperature: 73.6° F.-Stop Temperature: 73.8° F.

| RPM | Example II | Example IX | U Gold Plus | Spindle # |
|---|---|---|---|---|
| 5 | 940 | 802 | 244 | 1 |
| 10 | 595 | 501 | 240 | 1 |
| 20 | 374 | 315 | 234 | 1 |
| 50 | 247 | 210 | 230 | 2 |
| 100 | 156 | 141 | 224 | 2 |

Figure 4:
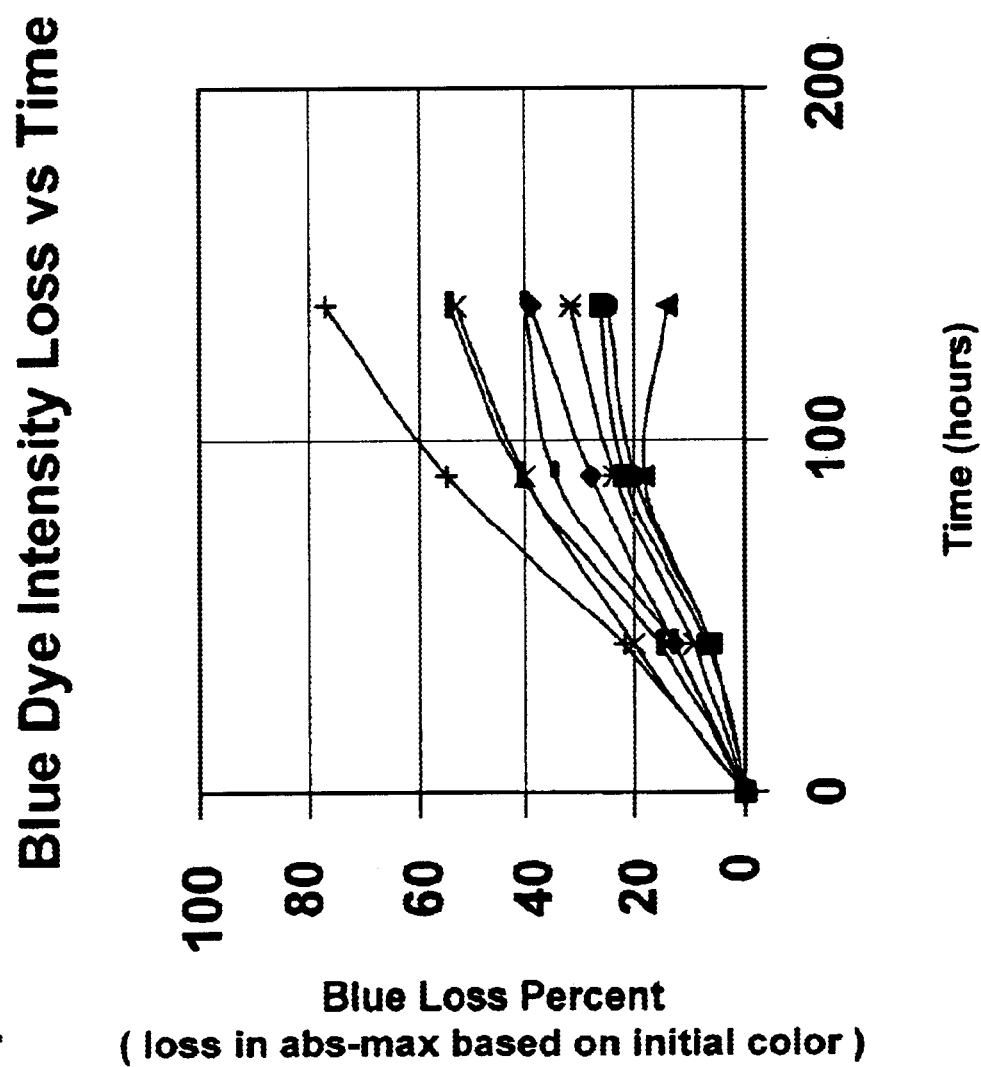
FIG. 4 is a graph showing the color stability of FD&C blue dye number 1 (using conventional colorimetric spectroscopic absorbance measurement). FD&C Blue #1 is a dye that is particularly unstable in the presence of oxidative chlorine species.

FIG. 4 shows the stability is color obtained using a combination of urea and an oxidizable organic dye, not a pigment, in the oxidative systems of the invention (see Examples XXIIA, XXIIIA AND XXIIIC).

The above specification, example and data provide a clear basis for understanding the operation of the compositions and methods of the invention. While the invention can be embodied in a variety of specific examples and processes, the invention resides in the claims hereinafter appended. In the claims, the proportions are expressed in parts by weight per each one hundred parts of the claimed antimastitis composition as a whole.

We claim:

1. A physically and chemically stable, visibly indicated, mastitis treatment composition that can effectively reduce microbial populations on contact with an animal skin for an extended period, said composition comprising a blended combination comprising:
    (a) an aqueous acidulant part comprising an activator acid, a rheology modifier or a pseudoplastic thickener, a chlorine dioxide stable visual indicator system selected from the group consisting of:
        (i) about 0.05–30 wt % of urea and about 0.001–10 wt % of a colorant, based on the weight of the blended composition; and
        (ii) about 0.001–50 wt %, based on the weight of the blended compostion, of a dispersed oil phase, wherein said oil phase contains about 0.001–50 wt % of an oil-soluble dye, based on the weight of said oil phase, and said oil phase is uniformly dispersed in a fine particle size in the blended composition and a major proportion of water; and
    (b) a chlorite part substantially free of organic component, consisting essentially of an alkali metal chlorite salt;
    wherein the composition exhibits a visual indicator for a period of at least 24 hours and the composition comprises a rheology that promotes cling to immobilize the composition on the animal skin surface and provides a barrier to environmental contamination.

2. The composition of claim 1 wherein the visual indicator system contains, in the blended composition, about 0.1 to 5.0 wt % of urea and about 0.005 to 2.0 wt % of a blue dye.

3. The composition of claim 2 wherein the blue dye comprises FD&C Blue No. 1.

4. The composition of claim 1 wherein the blended composition further comprises a first indicator dye having color instability in the presence of chlorite or chlorine dioxide such that the dye substantially loses color within about an hour of blending and a second dye that maintains an effective color for at least 24 hours after blending.

5. The composition of claim 1 wherein the indicator stability comprises about one week.

6. The composition of claim 1 wherein the indicator stability comprises about two weeks.

7. The composition of claim 1 wherein the oil phase contains a drying oil.

8. A physically and chemically stable visibly indicated mastitis treatment composition comprising a combined aqueous acidulant part and a chlorite part, the mastitis treatment composition can effectively reduce microbial populations on contact with an animal surface for an extended period of time,
   (a) said aqueous acidulant part comprising an activator acid comprising a phosphoric acid, lactic acid, glycolic acid or mixtures thereof, and a chlorine dioxide stable visual indicator system selected from the group consisting of:
      (i) about 0.05–30 wt % of urea and about 0.001–10 wt % of a colorant, based on the weight of the composition; and
      (ii) about 0.001–50 wt %, based on the weight of the composition, of a dispersed oil phase, wherein said oil phase contains about 0.001–50 wt % of an oil-soluble dye, based on the weight of said oil phase, and said oil phase is uniformly dispersed in a fine particle size in the composition; and stable in the combined mastitis treatment composition; and
   (b) said chlorite part substantially free of organic component, consisting essentially of an alkali metal chlorite salt;
wherein the composition exhibits a visual indicator for a period of at least 24 hours and the composition comprises a rheology that promotes cling to immobilize the composition on the animal skin surface and provides a barrier to environmental contamination.

9. The composition of claim 8 wherein the visual indicator system contains, in the composition, about 0.1 to 5.0 wt % of urea and about 0.005 to 2.0 wt % of a blue dye.

10. The composition of claim 9 wherein the blue dye comprises FD&C Blue No. 1.

11. The composition of claim 8 wherein the composition further comprises a first indicator dye having color instability in the presence of chlorite or chlorine dioxide such that the dye substantially loses color within about an hour of blending and a second dye that maintains an effective color for at least 24 hours after blending.

12. The composition of claim 8 wherein the indicator stability comprises about one week.

13. The composition of claim 8 wherein the indicator stability comprises about two weeks.

14. The composition of claim 8 wherein the oil phase contains a drying oil.

15. A physically and chemically stable visually indicated mastitis treating composition in an acidulant part and a chlorite part, that can effectively reduce microbial populations, on contact with a teat surface and for an extended period, said composition comprising:
   (a) an aqueous acidulant part comprising:
      (i) about 0.1 to 15 parts by weight of an organic or inorganic acid, or salts thereof, or mixtures thereof, the acid selected from the group consisting of a phosphoric acid, lactic acid, glycolic acid, a $C_{7-11}$ carboxylic acid, a $C_{6-12}$ alkyl benzene sulfonic acid, and mixtures thereof;
      (ii) a rheology modifier comprising about 0.01 to 10 parts by weight of a pseudoplastic thickener;
      (iii) a visual indicator system selected from the group consisting of:
         (a) about 0.05–30 wt % of urea and about 0.001–10 wt % of a colorant, based on the weight of the composition; and
         (b) about 0.001–50 wt %, based on the weight of the composition, of a dispersed oil phase, wherein said oil phase contains about 0.001–50 wt % of an oil-soluble dye, based on the weight of said oil phase, and said oil phase is uniformly dispersed in a fine particle size in the composition that can retain color stability for at least 24 hours in the presence of chlorite or chlorine dioxide;
      (iv) about 0.1 to 15 parts of an emollient;
      (v) a major proportion of water; and
   (b) a chlorite part consisting essentially of an alkali metal chlorite salt;
wherein the composition exhibits rheology that promotes cling to immobilize the composition on the teat surface and provides a barrier to environmental contamination.

16. The composition of claim 15 wherein the alkali metal chlorite salt is sodium chlorite and the organic acid is lactic acid.

17. The composition of claim 15 additionally comprising about 0.01 to 8 parts of a polymeric film-forming agent.

18. The composition of claim 15 wherein the visual indicator contains about 0.01 to 2 wt % urea.

19. The composition of claim 15 wherein the visual indicator system comprises, in the composition, about 0.05 to 0.001 wt % of urea and about 0.001 to 10 wt % of a blue dye.

20. The composition of claim 19 wherein the visual indicator system contains FD&C Blue No. 1.

21. The composition of claim 15 wherein the composition further comprises a first indicator dye having color instability in the presence of chlorite or chlorine dioxide such that the dye substantially loses color within about an hour of blending and a second dye that maintains an effective color for at least 24 hours after blending.

22. The composition of claim 15 wherein the indicator stability comprises about one week.

23. The composition of claim 15 wherein the indicator stability comprises about two weeks.

24. The composition of claim 21 wherein the oil phase contains a drying oil.

25. The composition of claim 15 wherein the organic acid is a $C_{7-11}$ carboxylic acid, a $C_{6-12}$ alkyl benzene sulfonic acid or mixtures thereof.

26. The composition of claim 15 wherein the composition further comprises a mixture of about 0.05 to 2 parts by eight of a xanthan thickener and about 0.1 to 5 parts by weight of a film-forming agent selected from the group consisting of a polyvinyl alcohol, a polyvinyl acetate and mixtures thereof.

27. The composition of claim 15 wherein the pH of the composition comprising the acidulant part and the chlorine part, is about 2.5 to 4.5.

28. The composition of claim 15 wherein the pH of the composition comprising the acidulant part and the chlorite part is about 2.5 to 3.5.

* * * * *